(12) United States Patent
Muni et al.

(10) Patent No.: US 10,959,949 B2
(45) Date of Patent: \*Mar. 30, 2021

(54) COMPOSITION AND METHOD FOR VANCOMYCIN ORAL LIQUID

(71) Applicant: Azurity Pharmaceuticals, Inc., Woburn, MA (US)

(72) Inventors: Indu Muni, North Reading, MA (US); Peter Mione, Malden, MA (US); Anisa Gandhi, Medford, MA (US); Cristina LeChiara, Saugus, MA (US)

(73) Assignee: Azurity Pharmaceuticals, Inc., Woburn, MA (US)

( \* ) Notice: Subject to any disclaimer, the term of this patent is extended or adjusted under 35 U.S.C. 154(b) by 60 days.

This patent is subject to a terminal disclaimer.

(21) Appl. No.: 16/941,414

(22) Filed: Jul. 28, 2020

(65) Prior Publication Data

US 2020/0352858 A1 Nov. 12, 2020

Related U.S. Application Data

(63) Continuation of application No. 15/126,059, filed as application No. PCT/US2015/020575 on Mar. 13, 2015.

(60) Provisional application No. 61/992,414, filed on May 13, 2014, provisional application No. 61/953,076, filed on Mar. 14, 2014.

(51) Int. Cl.
| | |
|---|---|
| *A61K 9/08* | (2006.01) |
| *A61K 47/12* | (2006.01) |
| *A23L 2/60* | (2006.01) |
| *A61K 38/14* | (2006.01) |
| *A23L 2/52* | (2006.01) |
| *A23L 2/56* | (2006.01) |
| *A61K 9/00* | (2006.01) |
| *A61K 47/26* | (2006.01) |

(52) U.S. Cl.
CPC ............... *A61K 9/08* (2013.01); *A23L 2/52* (2013.01); *A23L 2/56* (2013.01); *A23L 2/60* (2013.01); *A61K 9/0095* (2013.01); *A61K 38/14* (2013.01); *A61K 47/12* (2013.01); *A61K 47/26* (2013.01); *A23V 2002/00* (2013.01)

(58) Field of Classification Search
CPC ........................................................ A61K 9/08
See application file for complete search history.

(56) References Cited

U.S. PATENT DOCUMENTS

| | | | |
|---|---|---|---|
| 4,670,258 | A | 6/1987 | Harris et al. |
| 10,493,028 | B2 | 12/2019 | Muni et al. |
| 10,688,046 | B2 | 6/2020 | Muni et al. |
| 2003/0032600 | A1 | 2/2003 | Ulrich et al. |
| 2004/0191276 | A1 | 9/2004 | Muni et al. |
| 2010/0267624 | A1 | 10/2010 | De Tommaso et al. |
| 2011/0053877 | A1 | 3/2011 | Cakir et al. |
| 2013/0009330 | A1 | 1/2013 | Fragale et al. |
| 2014/0079777 | A1 | 3/2014 | Lord et al. |
| 2015/0238613 | A1 | 8/2015 | Lin et al. |
| 2016/0101147 | A1 | 4/2016 | Palepu et al. |
| 2017/0079910 | A1 | 3/2017 | Muni et al. |
| 2018/0116955 | A1 | 5/2018 | Muni et al. |
| 2020/0069584 | A1 | 3/2020 | Muni et al. |

FOREIGN PATENT DOCUMENTS

| | | |
|---|---|---|
| EP | 1357928 A2 | 3/2003 |
| JP | 2003-235497 A | 8/2003 |
| JP | 2004-535370 A | 11/2004 |
| JP | 2008-201778 A | 9/2008 |
| WO | WO 97/19690 A1 | 6/1997 |
| WO | WO 2006/020962 A2 | 2/2006 |
| WO | WO 2007/133711 A2 | 11/2007 |
| WO | WO 2012/094381 A2 | 7/2012 |
| WO | WO 2012/159103 A1 | 11/2012 |
| WO | WO 2014/010924 A1 | 1/2014 |
| WO | WO 2014/194296 A1 | 12/2014 |
| WO | WO 2015/138983 A1 | 9/2015 |

OTHER PUBLICATIONS

International Search Report and Written Opinion for International Application No. PCT/US2015/020575 dated Apr. 29, 2015.
International Preliminary Report on Patentability for International Application No. PCT/US2015/020575 dated Sep. 22, 2016.
Extended European Search Report for EP15761279.7 dated Dec. 1, 2017.
Notice of Paragraph IV Certification Re: Alkem Laboratories Ltd.'S Vancomycin Hydrochloride for Oral Solution, 25 Mg/Ml and 50 Mg/Ml; U.S. Pat. No. 10,493,028. Dated Jul. 7, 2020. 27 pages.
[No Author Listed], Vancomycin 50-Vancomycin 50 mg/mL in FIRST®-Grape Solution: Compounding Kit. Package Insert. Jan. 2014. 2 pages.
[No Author Listed], Vancomycin hydrochloride for injection, USP. Hospira, Inc. Package Insert. Oct. 2015. 13 pages.
[No Author Listed], Vancomycin Powder for Infusion 1g. EMC+. Feb. 2013. 9 pages.
Bartlett, Narrative review: the new epidemic of *Clostridium difficile*-associated enteric disease. Ann Intern Med. Nov. 21, 2006;145(10):758-64. Review.
Bartlett, The case for vancomycin as the preferred drug for treatment of *Clostridium difficile* infection. CID. 2005:46:1489-92.

(Continued)

*Primary Examiner* — Sarah Alawadi

(74) *Attorney, Agent, or Firm* — Wolf, Greenfield & Sacks, P.C.

(57) ABSTRACT

The invention relates to stable vancomycin hydrochloride powder for oral liquid formulations. Also provided herein are methods of using vancomycin oral liquid formulations for the treatment of certain diseases such as *Clostridium difficile* pseudomembranous colitis and Staphylococcal enterocolitis as well as kits and related products thereof.

10 Claims, 4 Drawing Sheets

(56) References Cited

OTHER PUBLICATIONS

Ensom et al., Stability of vancomycin 25 mg/mL in Ora-Sweet and water in unit-dose cups and plastic bottles at 4° and 25° C. Can J Hosp Pharm. 2010. 63(5):366-372.

Fraser et al., *Clostridium difficile.* Cleveland Clinic Center for Continuing Education. Feb. 2013. http://www.clevelandclinicmeded.com/medicalpubs/diseasemanagement/infectious-disease/clostridium-difficile-infection [last accessed Dec. 13, 2016].

Hull et al., *Clostridium difficile*-associated colitis. Can Fam Physician. 2004;50:1536-40.

Johnson et al., Treatment of asymptomatic *Clostridium difficile* carriers (fecal excretory) with vancomycin or metronidazole. A randomized, placebo-controlled trial. Ann Intern Med. Aug. 15, 1992;117(4):297-302.

Mallet et al., Storage of vancomycin oral solution. N Engl J Med. Aug. 12, 1982;307(7):445.

Pawar et al., *Clostridium difficile*-associated diarrhea: a review. Indian Med Gazette. Dec. 2011:145(12):481-94.

Weir et al., Protecting against Clostridium difficile illness. CMAJ. Apr. 26, 2005;172(9):1178.

Whaley et al., Stability of vancomycin in SyrSpend SF. Int J Pharm Compd. Mar.-Apr. 2012;16(2):167-9.

U.S. Appl. No. 16/988,387, filed Aug. 7, 2020, Muni et al.

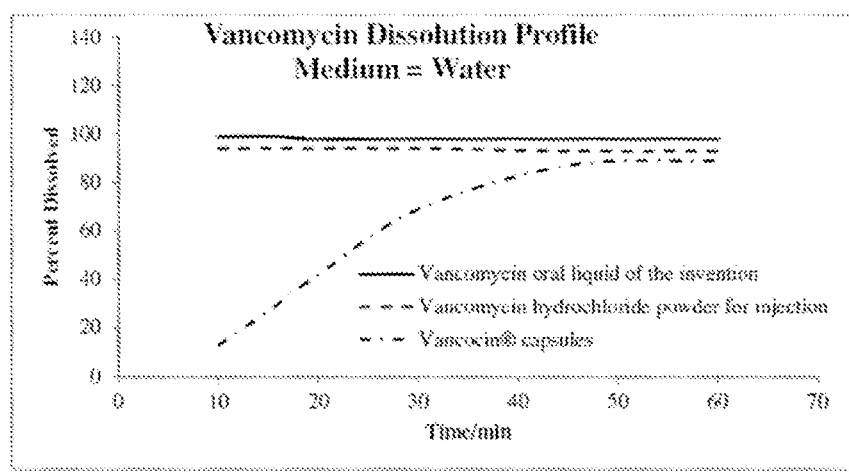
FIG. 3 Vancomycin Dissolution Profile in Water
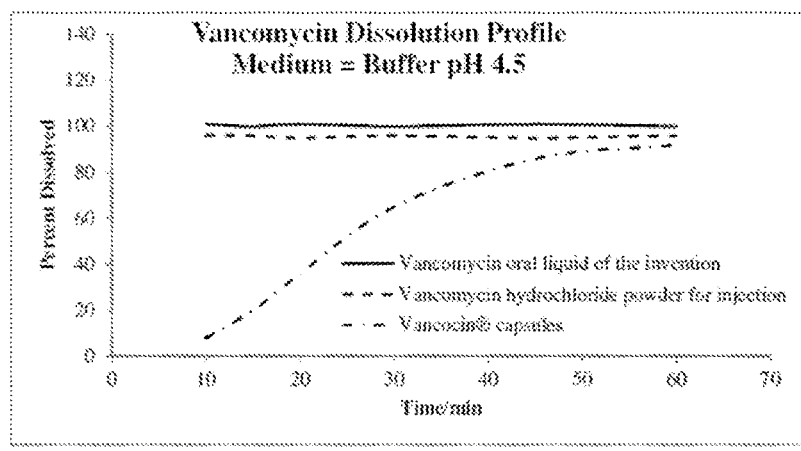
FIG. 4 Vancomycin Dissolution Profile in Buffer pH 4.5

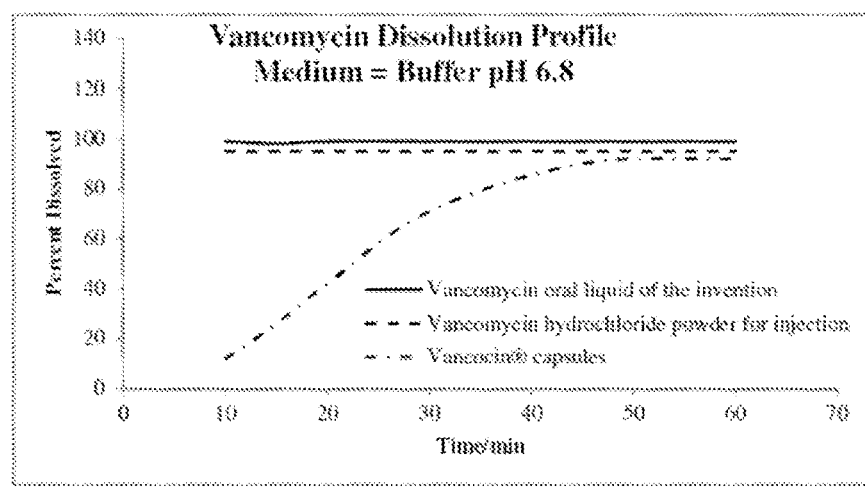
FIG. 5 Vancomycin Dissolution Profile in Buffer pH 6.8
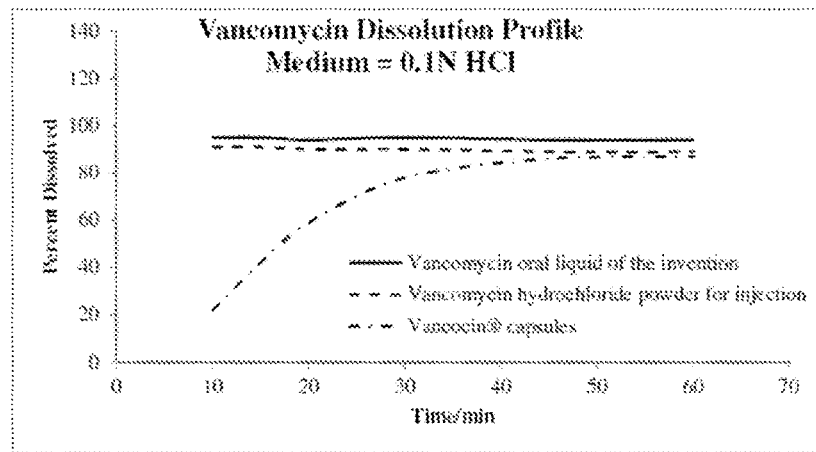
FIG. 6 Vancomycin Dissolution Profile in 0.1N HCl

COMPOSITION AND METHOD FOR VANCOMYCIN ORAL LIQUID

RELATED APPLICATIONS

This application is a continuation of U.S. application Ser. No. 15/126,059, filed Sep. 14, 2016, which is a national stage application of international application no. PCT/US2015/020575, filed Mar. 13, 2015 which claims the benefit of priority under 35 U.S.C. § 119(e) to U.S. Provisional Application Ser. No. 61/953,076, filed on Mar. 14, 2014, and U.S. Provisional Application Ser. No. 61/992,414, filed on May 13, 2014, both entitled "COMPOSITION AND METHOD FOR VANCOMYCIN ORAL LIQUID" each of which is herein incorporated by reference in its entirety.

BACKGROUND OF THE INVENTION

*Clostridium difficile*, commonly referred to as *C. diff.*, is a bacterium best known for causing antibiotic-associated diarrhea. The bacterium is known to cause infection when competing bacteria in the gut have been wiped out following the use of antibiotic treatment. Some people infected with *C. diff.* are asymptomatic, while others infected may experience severe diarrhea, abdominal pain, fever and a distinctive foul stool odor. *C. diff* infections are the most common cause of pseudomembranous colitis and in rare cases can progress to a life-threatening condition such as toxic megacolon. To date, *C. diff* is the most prevalent cause of infectious diarrhea and colitis in the United States.

*C. diff* was first described in 1935 as *Bacillus difficilis* following the analysis of fecal samples of healthy newborn infants, in a study conducted by Hall and O'Toole. The species name "*difficile*" remained due to the difficulty involved in the isolation and study of these bacteria. *C. diff* was later described as an obligate anaerobic, spore-producing, gram-positive rod, belonging to an ancient group of bacteria called the Clostridia, giving the name *Clostridium difficile*. Clostridia are motile bacteria that are especially prevalent in soil, but a commensal bacterium of the human intestine. In 1977, Bartlett identified it as an anaerobic bacterium, potent human pathogen and the etiologic agent responsible for antibiotic associated pseudomembranous colitis and recognized it as the major cause of antibiotic-associated diarrhea. *C. diff.* has since been recognized as a hospital-acquired infection (HAI) pathogen, inflicting morbidity in infected individuals triggered by the widespread use of the antibiotic clindamycin. Over the following years, the antibiotics in the penicillin and cephalosporin families contributed to the *C. diff.* epidemic.

*C. difficile* spores can live outside the body for long periods of time, and can be easily spread from patient to patient in healthcare facilities. Therefore, hospital patients, nursing home residents and individuals taking antibiotics are at higher risk for *Clostridium difficile* infection (CDI) due to the increased chance of exposure. The transfer of *C. diff* occurs via fecal-oral route where the spores pass through the stomach and ultimately end up in the colon. Once antibiotics are introduced, the normal enteric flora is suppressed making an environment in which *C. diff* can proliferate and produce *Clostridium difficile*-associated diarrhea (CDAD) through toxins A (enterotoxin) and B (cytotoxin). In terms of *C. diff,* approximately 3% of healthy adult stools test positive where the frequency of stool carriage increases to 16-35% in hospital patients.

When CDI is suspected, a test varies from institution to institution-stool culture, cytotoxin assay, PCR, ELISA, Latex agglutination assay for glutamate dehydrogenase or endoscopy are performed. The most common test used to diagnose *C. diff.* is ELISA to detect toxin A and B. Once CDI is diagnosed, treatment is administered. The top three medications prescribed are metronidazole, vancomycin, and fidaxomicin. First-line therapy, for mild to moderate *C. difficile* diarrhea, is restricted to metronidazole. Second-line therapy for severe infections and/or treatment failure is vancomycin. Intravenously-administered vancomycin should not be used for the treatment of *C. difficile* due to its inability to penetrate the colon and reach therapeutic concentrations via this route of administration. However, orally-administered vancomycin reaches very high concentrations in the colon (generally 500-1000 μg/mL) and cannot be absorbed; thus, oral vancomycin is a favorable choice for the treatment of *C. difficile* pseudomembranous colitis and Staphylococcal enterocolitis by being confined to the site of infection, and is then excreted fecally.

SUMMARY OF THE INVENTION

In some aspects the invention is a non-sterile stable liquid formulation of a compounded solution of vancomycin hydrochloride that is homogenous and stable for at least 30 days at ambient and refrigerated temperature conditions. In some embodiments the compounded solution of vancomycin is comprised of a liquid solution that is not Ora-sweet. In some embodiments ambient temperature is 22-28° C. In other embodiments ambient temperature is 25±2° C. In some embodiments the solution of vancomycin hydrochloride is homogenous and stable under ambient humidity. For instance, ambient humidity may be 60±5% relative humidity. In other embodiments refrigerated temperature is 2°-8° C.

In yet other aspects, the invention is a stable powder for compounding to produce a liquid formulation of a compounded solution of vancomycin hydrochloride, wherein the powder is stable for at least 30 days at ambient and refrigerated temperature conditions. In some embodiments the powder is stable for at least 6 months, 12 months, or 18 months at ambient temperatures.

In some embodiments the liquid solution is stable for up to 3 months at accelerated conditions. In some embodiments accelerated conditions are 35-45° C. and 68-78% relative humidity. In other embodiments accelerated conditions are 40° C. and 74% relative humidity. The liquid solution in yet other embodiments is stable for up to 24 months at ambient conditions.

The liquid solution in some embodiments includes one or more of, or in other embodiments, all of:
 (a) a buffering agent,
 (b) water,
 (c) a sweetener,
 (d) a flavoring agent,
 (e) a preservative, and
 (f) a dye.

The buffering agent in some embodiments is about 0.12% (w/v) citric acid (anhydrous). In other embodiments the sweetener is about 0.2% (w/v) sucralose. In yet other embodiments the flavoring agent is about 0.05% (w/v) artificial grape flavor. The preservative is about 0.05% (w/v) sodium benzoate in some embodiments. The preservative is about 0.1% (w/v) sodium benzoate in some embodiments. In other embodiments the preservative is about 0.1%-0.05% (w/v) sodium benzoate. The dye in some embodiments is about 0.0002% (w/v) D&C Yellow No. 10 and about 0.000038% (w/v) FD&C Red No. 40.

The compounded solution of the liquid formulation may be formulated for use in the treatment of different infectious agents including *C. difficile* pseudomembranous colitis and Staphylococcal enterocolitis.

In some embodiments the compounded solution is formulated to inhibit the growth of bacteria, mold and yeast for at least 30 days at ambient and refrigerated temperature conditions. In other embodiments the liquid solution is formulated to inhibit the growth of mold and yeast but not bacteria for greater than 30 days at room temperature conditions.

In other embodiments the concentration of vancomycin in the compounded solution is 1-100 mg/ml, 20-60 mg/ml, or 25-50 mg/ml.

A kit is provided in other aspects of the invention. The kit includes a first container comprising a non-sterile 100% (w/w) vancomycin hydrochloride powder, pre-measured into a respective unit of use amount, a second container comprising an oral liquid solution, pre-measured into a respective unit of use amount, and instructions for use, wherein the first and second containers are of a size such that the vancomycin hydrochloride powder and oral liquid solution can be combined in either the first or second container to produce a compounded solution of vancomycin hydrochloride, and wherein the compounded solution of vancomycin hydrochloride is homogenous and stable for at least 30 days at ambient and refrigerated temperature conditions.

In some embodiments the first or second container is a size to hold a 25 mg/mL or 50 mg/mL vancomycin oral liquid solution. In other embodiments the first container houses 3.84 g, 7.69 g, 10.76 g, or 15.38 g vancomycin hydrochloride (equivalent to 3.75 g, 7.5 g, 10.5 g, or 15 g vancomycin, respectively). The first or second container may be a size to hold a volume appropriate for therapy to treat *C. difficile* pseudomembranous colitis and/or Staphylococcal enterocolitis; 5 oz. (150 mL, as dispensed), 7 oz. (210 mL, as dispensed) and 10 oz. (300 mL, as dispensed).

In certain embodiments, the powder is comprised of vancomycin hydrochloride having microbial assay values of about 900 μg/mg or about 1100 μg/mg, compositions having about 85% vancomycin B and about 5% or less any other impurities or other substances and about 4.7% monodechlorovancomycin at the end of a given storage period. The powder does not, in some embodiments, contain any additional excipients such as glidants, sweeteners, or flavoring.

Also provided herein are processes for preparing a vancomycin oral liquid formulation. In one aspect, the process comprises the steps of (i) providing a uniform powder comprising 100% (w/w) vancomycin hydrochloride in a bottle; (ii) adding the entire bottle of water, sweeteners, flavoring agents, preservatives, and dye in liquid form (solution component); (iii) shaking the liquid formulation for about 30 seconds; and (iv) instructing the patient to shake the bottle well before each use.

A non-sterile stable liquid formulation of a compounded solution of vancomycin hydrochloride that is homogenous and stable for at least 30 days at ambient and refrigerated temperature conditions, wherein the compounded solution has a high solubility in water and a pH of about 2.5-4.5 is provided in other aspects of the invention. In some embodiments the compounded solution is an amber color. In other embodiments the compounded solution includes a sweetener.

In other aspects, the invention is a non-sterile stable liquid formulation comprising a compounded solution of vancomycin hydrochloride that has been dissolved in a liquid solution comprising a preservative, wherein the compounded solution is stable for at least 30 days at ambient and refrigerated temperature conditions and wherein the preservative is present in the liquid solution at a concentration range of 0.8-0.2% (w/v).

In another aspect the invention is a liquid solution comprising (a) 0.1-0.4% (w/v) citric acid (anhydrous), (b) water, (c) 0.1-0.3% (w/v) sucralose, (d) 0.01-0.1 (w/v) of a flavoring agent, (e) 0.08-0.02% (w/v) sodium benzoate, and (f) 0.0001-0.0003% (w/v) of a dye. In some embodiments the citric acid is 0.12% (w/v) of the solution. In other embodiments the sucralose is 0.2% (w/v) of the solution, the flavoring agent is 0.05% (w/v) artificial grape flavor, the sodium benzoate is about 0.05% (w/v) of the solution and/or the dye comprises about 0.0002% (w/v) D&C Yellow No. 10 and about 0.000038% (w/v) FD&C Red No. 40.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

FIG. 3 is a graph of dissolution profiles in water for three commercially available vancomycin products.

FIG. 4 is a graph of dissolution profiles in pH 4.5 buffer for three commercially available vancomycin products.

FIG. 5 is a graph of dissolution profiles in pH 6.8 buffer for three commercially available vancomycin products.

FIG. 6 is a graph of dissolution profiles in 0.1 N HCl for three commercially available vancomycin products.

DETAILED DESCRIPTION

Figure 1:
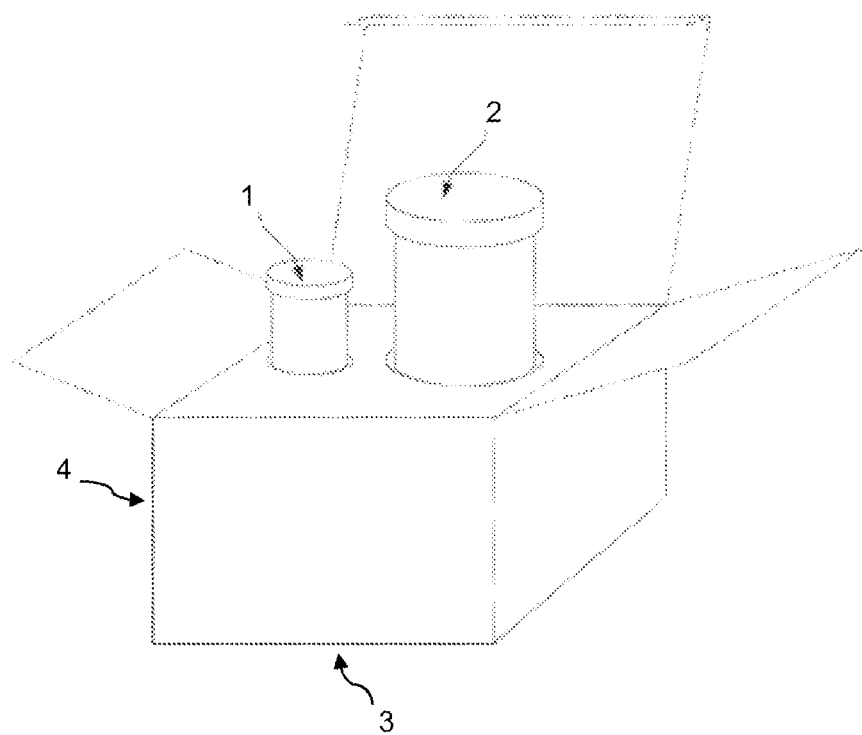
FIG. 1 illustrates exemplary components of a kit of the invention.

The invention encompasses liquid compounded formulations of Vancomycin hydrochloride powder as well as related compounding kits. The liquid formulations have enhanced stability with respect to available liquid formulations. As is well known in the art compounded formulations include reconstituted formulations.

Also provided herein are methods of treating *Clostridium difficile* pseudomembranous colitis and Staphylococcal enterocolitis comprising administering to a patient, such as a child or an elderly patient, an oral liquid formulation compounded from vancomycin hydrochloride powder as described herein.

Commonly, pediatric and geriatric populations encounter difficulty being administered solid oral dosage forms such as capsules. This may lead to non-compliance with the recommended pharmacotherapy with the solid oral dosage forms and likely results in rendering the therapy ineffective. Solid oral dosage forms are usually not favorable for pediatric and geriatric populations due to the potential risk of choking. Additionally, certain solid oral dosage forms of medications cannot be administered simply by crushing (e.g., patients requiring various types of feeding tubes) because of the coating or drug delivery mechanism by which the drug is released. Alternatively, vancomycin hydrochloride powder for injection is typically mixed with sterile water for injection as a more cost-effective and accessible option for children, the elderly, and patients with feeding tubes in comparison to the oral capsules. For most community pharmacies (retail/chain, independent, and the like), vancomycin hydrochloride powder for injection as well as sterile water for injection are not always readily available and expensive vancomycin hydrochloride oral capsules are usually dispensed.

The current method of overcoming the aforementioned drawbacks of the solid oral dosage form of vancomycin hydrochloride is mixing multiple vials of vancomycin hydrochloride powder for injection with multiple vials of sterile water for injection to achieve the prescribed concentration. This method of preparation is cumbersome and time-consuming for pharmacists in today's busy pharmacies. Oftentimes, this formulation is not flavored to mask the unpalatable bitterness of vancomycin hydrochloride; thus, this can significantly lead to a decrease in patient compliance. Additionally, another disadvantage with the current method of compounding vancomycin oral solution, and with many compounds, is the potential for contamination. As noted, sterile water for injection is typically the vehicle for compounding this preparation and it lacks preservatives. In a study conducted by Mallet et al (1982), a precipitate had been documented on day 6 of observation at room temperature in the vancomycin oral solution mixed with distilled water, which also lacks preservatives. For patients already ill with a staphylococcal or C. difficile infection, any other types of pathogens (e.g., bacteria, viruses, fungi/yeast, and/or mold spores) could potentially worsen their intended therapeutic outcome due to the administration and/or shortening of therapy resulting from the contaminated product.

The methods and products of the invention overcome the difficulties arising from prior art methods of administering vancomycin hydrochloride. The compositions provide a number of advantages over conventional oral vancomycin hydrochloride capsules, as well as vancomycin hydrochloride powder for injection vials mixed with sterile water for injection. For instance, the enhanced stability allows for the preparation of compounded solutions for longer term administration protocols. The compounded solutions also have enhanced accessibility to children and the elderly, increased patient compliance to medication, and increased protection against the growth of accidentally introduced yeast and/or mold. The compounded solutions of the invention allow for the safe and effective oral administration of vancomycin hydrochloride for the treatment of severe and/or recurrent infections of *Clostridium difficile* pseudomembranous colitis and Staphylococcal enterocolitis.

Vancomycin hydrochloride is commercially available in the form of oral capsules (e.g., Vancocin®, and also generic) and lyophilized powder for injection. Vancomycin hydrochloride powder for injection (e.g., Vancocin®, and also generic), a sterile powder, is typically mixed with sterile water for injection and, occasionally, with other ingredients such as sweeteners and/or flavoring agents to be administered as a compounded oral solution. Currently, there is no commercially available vancomycin hydrochloride powder for oral liquid formulation to provide multiple and flexible (MultiFlex™) dosing which may be used for all populations and various indications. The invention provides such a compounded solution.

As used herein, "vancomycin" refers to vancomycin base, its salt, or solvate or derivative or isomer or polymorph thereof. Suitable compounds include the free base, the organic or inorganic salts, isomers, isomer salts, solvates, polymorphs, complexes, etc. U.S. Pat. No. 4,670,258 discloses an exemplary method in the preparation, stability, and storage of vancomycin oral liquid. In some embodiments, the vancomycin used in the compositions described herein is a vancomycin salt, vancomycin hydrochloride.

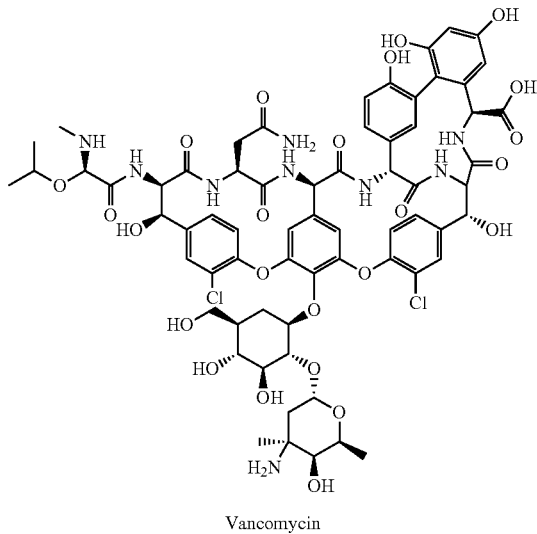

Vancomycin

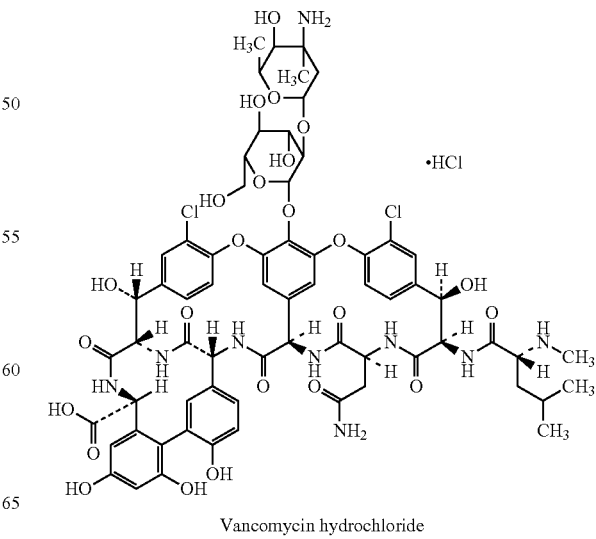

Vancomycin hydrochloride

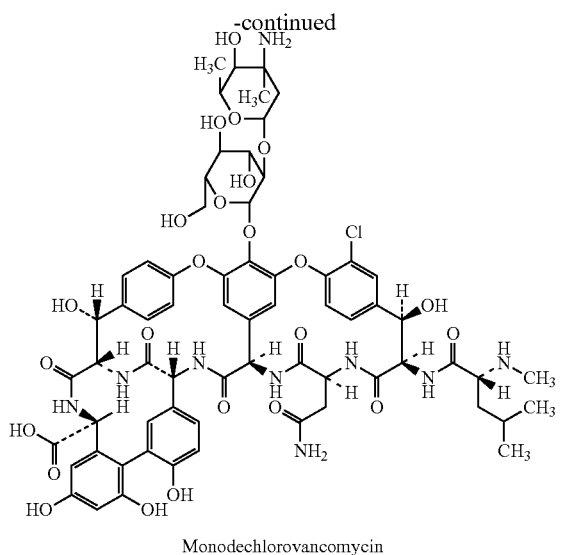

Monodechlorovancomycin

The liquid formulations and/or kits described herein may include additional ingredients. For instance these additional components may include, but are not limited to, buffering agents, preservatives, sweeteners, flavoring agents, coloring agents. Additional excipients such as tonicity agents and chelating agents are within the scope of the embodiments. The compounded solution of the invention is prepared by mixing a powder form of vancomycin hydrochloride with a liquid solution, also referred to as a diluent. The liquid solution or diluent of the invention imparts improved properties on the compounded solution. It was discovered quite surprisingly that an optimal liquid solution can impart on the compounded solution enhanced stability at room temperature without interfering with the activity of the vancomycin hydrochloride. An example of the optimal liquid solution is presented below:

(a) 0.1-0.4% (w/v) citric acid (anhydrous),
(b) water,
(c) 0.1-0.3% (w/v) sucralose,
(d) 0.01-0.1 (w/v) of a flavoring agent,
(e) 0.08-0.2% (w/v) sodium benzoate, and
(f) 0.0001-0.0003% (w/v) of a dye.

Buffering agents maintain the pH when vancomycin hydrochloride powder is compounded into a liquid form. Non-limiting examples of buffering agents include, but are not limited to, sodium bicarbonate, potassium bicarbonate, magnesium hydroxide, magnesium lactate, magnesium gluconate, aluminum hydroxide, aluminum hydroxide/sodium bicarbonate precipitate, a mixture of an amino acid and a buffer, a mixture of aluminum glycinate and a buffer, a mixture of acid salt and an amino acid and a buffer, and a mixture of an alkali salt of an amino acid and a buffer. Additional buffering agents include citric acid, sodium citrate, sodium tartarate, sodium acetate, sodium carbonate, sodium polyphosphate, potassium polyphosphate, sodium pyrophosphate, potassium pyrophosphate, disodium hydrogenphosphate, trisodium phosphate, tripotassium phosphate, sodium acetate, potassium metaphosphate, magnesium oxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is compounded into a liquid. In some embodiments, the vancomycin hydrochloride powder described herein, when compounded into a liquid form, comprises a buffering agent.

Preservatives include anti-microbials, anti-oxidants, and agents that enhance sterility. Exemplary preservatives include ascorbic acid, ascorbyl palmitate, benzyl alcohol, BHA, BHT, citric acid, erythorbic acid, fumaric acid, malic acid, propyl gallate, sodium ascorbate, sodium benzoate, sodium bisulfate, sodium metabisulfite, sodium sulfite, parabens (methyl-, ethyl-, butyl-), benzoic acid, potassium sorbate, and vanillin. In some embodiments, the vancomycin hydrochloride powder described herein, when compounded into a liquid form, comprises a preservative.

Sweeteners or sweetening agents include any compounds that provide a sweet taste to make the product more palatable. This includes natural and synthetic sugars, natural and artificial sweeteners (e.g., sucralose), natural extracts and any material that initiates a sweet sensation in a subject. In some embodiments, the vancomycin hydrochloride powder described herein, when compounded into a liquid form, comprises a sweetener. In other embodiments, sweeteners in liquid form are used to solvate or dissolve the vancomycin hydrochloride powder described herein.

Sugars illustratively include glucose, fructose, sucrose, xylitol, tagatose, maltitol, isomaltulose, lactitol, sorbitol, mannitol, erythritol, trehalose, maltodextrin, polydextrose, and the like. Other sweeteners include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrosylates, maltitol syrup, high fructose corn syrup, and as branded proprietary blend products. Sweeteners can be used singly or combinations of two or more. Suitable concentrations of different sweeteners can be selected based on published information, manufacturers' data sheets, and by routine testing. In certain instances, an above-described flavored solution component is used to solvate or dissolves the vancomycin hydrochloride powder described herein.

In another embodiment, the liquid form comprises a flavoring agent or flavorant to enhance the taste or aroma of the solution component used to solvate or dissolve the vancomycin hydrochloride powder described herein. Suitable natural or synthetic flavoring agents can be selected from standard reference books, such as Remington: The Science and Practice of Pharmacy (2000) and *Fenaroli's Handbook of Flavor Ingredients* (1994). Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. Also useful, particularly where the composition is intended primarily for pediatric use is tutti-frutti or bubble gum flavor, a compounded flavoring agent based on fruit flavors. Presently, preferred flavoring agents include bubble gum, strawberry, cherry, grape, orange, peppermint, and vanilla. In some embodiments, the resultant liquid form from the vancomycin hydrochloride powder described herein comprises a grape (specifically, white grape) flavoring agent. According to pharmacist surveys that have been conducted, grape was among the most popular flavoring agents to be used for the compounding of oral vancomycin liquid (Vancomycin Survey Results, 2013; Pharmacist Compounding Study, 2012). Flavoring agents may be used singly or in combinations of two or more.

In further embodiments, the resultant liquid form from the vancomycin hydrochloride powder described herein comprises a coloring agent for identity and/or aesthetic purposes. Suitable coloring agents approved by the U.S. Food and Drug Administration (FDA) include FD&C Red No. 3, FD&C Red No. 20, FD&C Red No. 40, FD&C Yellow No. 6, FD&C Blue No. 2, D&C Green No. 5, D&C Orange No. 5, D&C Yellow No. 10, caramel, ferric oxide and mixtures thereof. The resultant liquid form from the vancomycin hydrochloride powder described herein displays an amber-colored appearance for identity and aesthetic purposes associated with a white grape flavor.

The vancomycin hydrochloride powder described herein is stable in various storage conditions including refrigerated, ambient, and accelerated conditions. Stable as used herein refer to vancomycin hydrochloride powder having microbial assay values of greater than 900 or in some embodiments about 1100 μg/mg, compositions having about 85% vancomycin B and about 5% or less any other impurities or other substances and about 4.7% monodechlorovancomycin at the end of a given storage period. Stability may be assessed by cylinder-plate assay (the cylinder plate assay depends on the diffusion of the antibiotic from a vertical cylinder through a solidified agar layer in a petri dish or plate. The growth of the specific microorganisms inoculated into the agar is prevented in a circular area or zone around the cylinder containing the solution of the antibiotic), HPLC or any other known testing method. In some embodiments, the stable vancomycin hydrochloride powder have microbial assay values of greater than 900, about 1100 μg/mg, about 1050 μg/mg, or about 1000 μg/mg. In some embodiments, the stable vancomycin hydrochloride has composition of about 85%, about 86%, about 87%, about 88%, about 89%, about 90%, about 91%, about 92%, about 93%, about 94%, about 95%, about 96%, about 97%, about 98%, or about 99% vancomycin B. In some embodiments, the stable vancomycin hydrochloride powder has about 5%, about 4%, about 3%, about 2.5%, about 2%, and 1.5%, about 1%, or about 0.5% individual impurities or substances. In yet other embodiments, the stable vancomycin hydrochloride powder has about 4.7%, about 4.5%, about 4.0%, about 3.5%, about 3.0%, about 2.5%, about 2.0%, about 1.5%, about 1.0%, or about 0.5% monodechlorovancomycin at the end of a given storage period.

At ambient conditions, the vancomycin hydrochloride powder described herein is stable, in some embodiments, for at least 1 month, at least 2 months, at least 3 months, at least 6 months, at least 9 months, at least 12 months, at least 15 months, at least 18 months, or at least 24 months. In other embodiments, at accelerated conditions, the vancomycin hydrochloride powder described herein is stable for at least 1 month, at least 2 months or at least 3 months. Accelerated conditions include temperature and/or relative humidity (RH) that are above ambient levels (e.g. 25±5° C.; 55±10% RH). In some instances, an accelerated condition is at about 30° C., about 35° C., about 40° C., about 45° C., about 50° C., about 55° C., or about 60° C. In other instances, an accelerated condition is above 65% RH, about 70% RH, about 75% RH, or about 80% RH. In further instances, an accelerated condition is about 40° C. or 60° C. at ambient humidity. In yet further instances, an accelerated condition is about 40° C. at 75±5% RH humidity. Ambient conditions include temperature and/or relative humidity (RH) that are at ambient levels (e.g. 25±5° C.; 55±10% RH. In some instances, an ambient condition is at about 20° C., about 21° C., about 22° C., about 23° C., about 24° C., about 25° C., about 26° C., about 27° C., about 28° C., about 29° C., and about 30° C. In other instances, an ambient condition is about 45% RH, about 50% RH, about 55% RH, about 60% RH, or about 65% RH. Refrigerated conditions include temperature and/or relative humidity (RH) in typical refrigeration units (e.g. 5±3° C.). In some instances, a refrigerated condition is about 2° C., about 3° C., about 4° C., about 5° C., about 6° C., about 7° C., or about 8° C.

The vancomycin hydrochloride powder described herein may be used for the preparation or compounding of a vancomycin oral liquid. As provided in the United States Pharmacopoeia (USP), oral liquids include, but are not limited to, aqueous and nonaqueous solutions, suspensions, syrups, emulsions, elixirs, etc. It is envisioned that solutions are also included where certain components of the vancomycin oral liquid compositions described herein are in solution or suspension. To exemplify, when a vancomycin hydrochloride powder is compounded with the inactive ingredients of the aqueous solution component, the vancomycin hydrochloride powder particles disperse into the liquid form (e.g., solution, suspension, etc.). Upon shaking the bottle containing the final product, the vancomycin hydrochloride powder particles are dispersed throughout the liquid form to provide a homogenous solution for consistent, accurate dosing for the patient. In some embodiments, the liquid form is a suspension. A thickening agent, or suspending agent, may be added to prepare a suspension from a solution. Suspensions consist of flocculated particles, often containing the active ingredient, which are dispersed throughout the medium upon stirring, shaking, swirling, agitation, inversion, or a combination thereof. However, suspensions can cause the active ingredient to settle on the bottom of its container after standing for a period of time. Therefore, if not appropriately shaken, stirred, etc., inaccurate dosing for the patient may occur. Furthermore, patients who require feeding tubes may experience clogging during administration which also significantly contributes to rendering the pharmacotherapy ineffective. Solutions are homogenous mixtures by which particles and/or molecules of the solute(s) (e.g., solids, liquids, or gases) are dissolved and uniformly dispersed throughout the solvent. Though suspensions and solutions have their own advantages, the uniformity of a solution assures accurate dosage upon administration; thus, this makes for a more preferred dosage form and will less likely be problematic when administering through feeding tubes.

Liquid vehicles suitable for the vancomycin hydrochloride powder described herein are selected for a particular oral liquid composition (e.g., solution, suspension, etc.) as well as other properties such as clarity, viscosity, compatibility with excipients, chemical inertness, palatability, odor, and color. Exemplary liquid vehicles include water, ethyl alcohol, glycerin, propylene glycol, syrup (e.g., sugar or other sweetener based, e.g., Ora-Sweet® SF sugar-free flavored syrup), juices (e.g., apple, orange, cranberry, cherry, tomato and the like), other beverages (e.g., tea, coffee, soft drinks, milk and the like), oils (e.g., olive, soybean, corn, mineral, castor and the like), and combinations or mixtures thereof. Certain liquid vehicles, e.g., oil and water, can be combined together to form emulsions. In some embodiments, water is used as a vehicle for a vancomycin oral liquid. In other embodiments, syrup is used as a vehicle for a vancomycin oral liquid. For the vancomycin hydrochloride powder described herein, the solution component is used as the vehicle for a vancomycin oral liquid.

Mixing methods encompass any type of mixing that result in a homogenous vancomycin liquid composition. In some embodiments, a quantity of a vancomycin hydrochloride powder is added to a liquid vehicle and then mixed by a stirring, shaking, swirling, agitation, inversion, or a combination thereof. In certain instances, a liquid vehicle is added to a quantity of a vancomycin hydrochloride powder in a container (e.g., a bottle, vial, bag, beaker, syringe, or the like). The container is then mixed by stirring, shaking, swirling, agitation, inversion, or a combination thereof. In certain instances, a fractional volume of the liquid vehicle (e.g., one-half, one-third, one-fourth volume, etc.) is added to a vancomycin hydrochloride powder, mixed by stirring, shaking, swirling, agitation, inversion, or a combination thereof; and, the subsequent liquid fraction(s) is added and mixed. In certain instances, one-half fractional volume of liquid is added to a vancomycin hydrochloride powder in a container and mixing by shaking; the other one-half fractional volume of the liquid vehicle is then subsequently added and mixed. In any of the above embodiments, mixing (e.g., stirring, shaking, swirling, agitation, inversion, or a combination thereof) occurs for specific time intervals such as about 10 seconds, about 20 seconds, about 30 seconds, about 45 seconds, about 60 seconds, about 90 seconds, about 120 seconds, about 2.5 minutes, about 3 minutes, about 3.5 minutes, about 4 minutes, or about 5 minutes. In embodiments, where there are two or more mixing steps, the time intervals for each mixing can be the same (e.g., 2×60 seconds) or different (e.g., 60 seconds for the first mixing and 30 seconds for the second mixing).

The vancomycin oral liquid compositions described herein are stable in various storage conditions including refrigerated and ambient conditions. Stable compositions as used herein refer to vancomycin oral liquid compositions having at least 98% vancomycin at the end of a given storage period. In some embodiments stable compositions have at least 85%, 90%, 93%, 95%, 96%, 97%, or 99% vancomycin at the end of a given storage period. Stability may be assessed by functional microbial assays or any other known testing method. In some embodiments, the stable vancomycin oral liquid compositions have at least about 98%, at least about 99%, at least about 100%, at least about 101%, at least about 102%, at least about 103%, at least about 104%, at least about 105%, at least about 106%, at least about 107%, at least about 108%, at least about 109%, at least about 110%, at least about 111%, at least about 112%, at least about 113%, at least about 114%, at least about 115% Vancomycin at the end of a given storage period using a functional microbial assay. Since the assay assesses actual versus theoretical microbial count, the percent of active vancomycin measured in the solution may exceed 100%. As shown in Example 4, the results indicate that the vancomycin oral liquid composition when stored at refrigerated (2-8° C.) conditions is stable for at least 30 days. In some embodiments, the stable vancomycin oral liquid composition have at least about 96.9% vancomycin at the end of a given storage period using a chemical assay.

At refrigerated and ambient conditions, in some embodiments, the vancomycin oral liquid compounding compositions described herein are stable for at least 1 week, 2 weeks, 3 weeks, 4 weeks, 5 weeks, or at least 6 weeks. Ambient conditions include temperature and/or relative humidity (RH) that are at ambient levels (e.g. 25±5° C.; 55±10% RH). In some instances, an ambient condition is at about 20° C., about 21° C., about 22° C., about 23° C., about 24° C., about 25° C., about 26° C., about 27° C., about 28° C., about 29° C., and about 30° C. In other instances, an ambient condition is about 45% RH, about 50% RH, about 55% RH, about 60% RH, or about 65% RH. Refrigerated conditions include temperature and/or relative humidity (RH) in typical refrigeration units (e.g. 5±3° C.). In some instances, a refrigerated condition is about 2° C., about 3° C., about 4° C., about 5° C., about 6° C., about 7° C., or about 8° C. In other embodiments the liquid solutions are stable at ambient and refrigerated conditions for several months.

For the vancomycin hydrochloride powder and liquid compositions described herein, kits and articles of manufacture are also described.

Kits may include vancomycin hydrochloride powder equivalent to 1 mg to 100 mg/mL vancomycin, more preferably 5 mg to 20 mg/mL vancomycin, more preferably 10 mg to 75 mg/mL, more preferably 20 mg to 60 mg/mL, and most preferably 25 mg/mL and 50 mg/mL.

Kits may be packaged to prepare volumes appropriate for required therapy, also referred to as unit of use containers. Exemplary volumes include 1 ounce (30 mL) to 20 ounces (600 mL), more preferably 3 ounces (60 mL) to 15 ounces (450 mL), and most preferably 5 ounces (150 mL), 7 ounces (210 mL), and 10 ounces (300 mL). The typical treatment for *C. difficile* pseudomembranous colitis and/or Staphylococcal enterocolitis can be 1 day, 2 days, 3 days, 4 days, 5 days, 6 days, 7 days, 8 days, 9 days, 10 days, 11 days, 12 days, 13 days, 14 days, and/or longer for recurrent infections, according to a survey study among pharmacists in various practice settings (Vancomycin Volume Study, April 2013).

An exemplary kit is shown in FIG. 1. Such kits can include a first container (1), a second container (2), a packaging material (3), and instructions for use (4) either included within the package or on the package. The package may be compartmentalized to receive one or more bottles and the like, each of the container(s) comprising of one of the separate elements to be used in a method described herein including a vancomycin hydrochloride powder or solution component. The suitable containers can be formed from a variety of materials including plastic materials.

A kit will typically be comprised of one or more additional containers, each one with one or more of various materials (such as vancomycin hydrochloride powder and solution component containing inactive ingredients) desirable from a commercial and user standpoint for a vancomycin hydrochloride powder or solution component herein. Non-limiting examples of such materials include, but not limited to, buffers, diluents, tools; carrier, package, container, and/or bottle labels listing contents, and package inserts with a set of instructions for compounding are included.

A label can be on or associated with the container. A label can be on a container when letters, numbers, or characters forming the label are attached or stamped onto the container itself; a label can be associated with a container when it is present within a receptacle or carrier that also holds the container, e.g., as a package insert.

The vancomycin oral liquid compositions may be used for the treatment of diseases and conditions described herein. In addition, a method for treating any of the diseases or conditions described herein in a subject in need of such treatment involves administration of vancomycin oral liquid compositions in therapeutically effective amounts to the subject. In some embodiments, the amount of a given vancomycin oral liquid composition that corresponds to such an amount varies depending on factors such as the particular vancomycin salt or form, disease condition and its severity, the identity (age, weight, sex) of the subject or patient in need of treatment, but can nevertheless be determined according to the particular circumstances surrounding the case, including, e.g., the specific agent being administered, the liquid composition type, the condition being treated, and the subject or patient being treated.

In further embodiments, the daily dosages appropriate for the vancomycin oral liquid compositions described herein are from about 40 mg/kg per body weight. In one embodiment, the daily dosage appropriate for the vancomycin liquid compositions is about 500 mg to 2 g.

In some embodiments, the vancomycin oral liquid compositions described herein are for the treatment of severe and/or recurrent infections of *Clostridium difficile* pseudomembranous colitis.

The treatment of certain diseases or conditions (e.g., *C. difficile* pseudomembranous colitis, Staphylococcal enterocolitis, etc.) in a patient or subject with a vancomycin oral liquid composition described herein encompass additional therapies and treatment agents in some embodiments. Such additional therapies and treatment regimens include another therapy, e.g., additional antibiotics, for the treatment of the particular disease in some embodiments.

Unless defined otherwise, all technical and scientific terms used herein have the same meanings as commonly understood by one of ordinary skill in the art. Although any methods and materials similar or equivalent to those described herein can be used in the practice of testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as oral vancomycin is directed to the treatment and/or the amelioration of, reversal of, or stabilization of the symptoms of *Clostridium difficile* pseudomembranous colitis and/or Staphylococcal enterocolitis described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an oral vancomycin composition, can include, but is not limited to, providing an oral vancomycin composition into or onto the target tissue; providing an oral vancomycin composition systemically to a patient by, e.g., oral administration whereby the therapeutic reaches the target tissue or cells. "Administering" a composition may be accomplished by injection, topical administration, and oral administration or by other methods alone or in combination with other known techniques.

As used herein, the term "container" or "containers" may mean bottles, vials, jars, pouches, and the like.

As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In certain instances, the human is elderly. In other instances, the human is 65 years of age or older. Other examples of subjects include experimental animals such as mice, rats, dogs, cats, goats, sheep, pigs, and cows. The experimental animal can be an animal model for a disorder, e.g., a transgenic mouse with *Clostridium difficile* pseudomembranous colitis and Staphylococcal enterocolitis pathology. A patient can be a human suffering from *Clostridium difficile* pseudomembranous colitis, Staphylococcal enterocolitis, or its variants or etiological forms.

By "pharmaceutically acceptable", it is meant the carrier, diluent or excipient must be compatible with the other ingredients of the formulation and not deleterious to the recipient thereof.

The term "pharmaceutical composition" shall mean a composition comprising of at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a composition of the present disclosure may be used to inhibit, block, or reverse the activation, migration, or proliferation of cells or to effectively treat *Clostridium difficile* pseudomembranous colitis and/or Staphylococcal enterocolitis or ameliorate the symptoms of *Clostridium difficile* pseudomembranous colitis and/or Staphylococcal enterocolitis.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Stability of Vancomycin Hydrochloride Powder

The stability of vancomycin hydrochloride powder was evaluated. 10 g of powder was placed in 325 mL HDPE (high density poly ethylene) bottle and stored under 25° C./60% Relative Humidity (RH) and 40° C./75% RH. At various time points the powder in the bottle was analyzed for vancomycin hydrochloride, vancomycin B, other impurities, and monodechlorovancomycin by HPLC or cylinder plate analysis. The following tables depict the stability of vancomycin hydrochloride in the bottle at the various storage conditions.

| μg/mg vancomycin hydrochloride powder | |
|---|---|
| Time (Months) | 40° C. /75% RH |
| 0 | 1067 mcg/mg |
| 1 | 1076 mcg/mg |
| 2 | 1097 mcg/mg |
| 3 | 1094 mcg/mg |
| 6 | 1137 mcg/mg |

| % Vancomycin B powder in bottle | | |
|---|---|---|
| Time (Months) | 25° C./60% (RH) | 40° C./75% RH |
| 0 | 93.03% | 93.03% |
| 1 | — | 91.87% |
| 2 | — | 89.14% |
| 3 | 92.19% | 88.22% |
| 6 | 92.04% | 81.84% |
| 9 | 89.34% | — |
| 12 | 88.85% | — |
| 18 | 90.8% | — |

| % other impurities powder in bottle | | |
|---|---|---|
| Time (Months) | 25° C./60% (RH) | 40° C./75% RH |
| 0 | <5.0% for all other | <5.0% for all other |
| 1 | — | <5.0% for all other |
| 2 | — | <5.0% for all other |
| 3 | <5.0% for all other | <5.0% for all other |
| 6 | <5.0% for all other | <5.0% for all other |
| 9 | <5.0% for all other | — |
| 12 | <5.0% for all other | — |
| 18 | <5.0% for all other | — |

| % Monodechlorovancomycin powder in bottle | |
|---|---|
| Time (Months) | 40° C./75% RH |
| 1 | 1.0% |
| 2 | 1.3% |
| 3 | 1.6% |

Based on the powder in bottle stability at ambient and accelerated conditions (25° C./60% RH and 40°/75% RH), it was determined that the vancomycin hydrochloride powder was stable.

Example 2: Stability of Prepared Vancomycin Oral Liquid 50 mg/mL vancomycin oral liquids were prepared from vancomycin hydrochloride made with the addition of the solution component and placed under refrigerated and 25° C./60% RH—ambient conditions. The following tables depict the stability of vancomycin oral liquid at various storage conditions.

| | % vancomycin | |
| | Vancomycin Oral Liquid | |
| Time (Days) | Refrigerated | 25° C./60% (RH) |
| --- | --- | --- |
| 0 | 109.7% | 109.7% |
| 14 | 109.2% | 109.8% |
| 30 | 110.0% | 109.4% |

In the prepared liquids, the vancomycin oral liquid was most stable at refrigerated and 25° C./60% RH conditions.

Example 3: Reconstitution Method

The overall mixing efficiency and solution drug concentration was evaluated. 289 mL of the solution component was added to a 325 mL bottle containing 15.38 g of vancomycin hydrochloride powder and the bottle was vigorously shaken for 30 seconds.

The resultant liquid was a clear amber solution. (The amber color is due to a color additive to the solution component.) The vancomycin hydrochloride powder easily dissolves in the solution component.

Example 4: Additional Stability Studies

Vancomycin hydrochloride was further investigated in stability studies. 15.38 g of vancomycin hydrochloride powder in 325 mL white plastic bottled were examined for stability in 25±2° C./60±5% RH for up to 3 months and 40±2° C./75±5% RH (accelerated) conditions up to 3 months. At each given time point, vancomycin hydrochloride, vancomycin B, other impurities, and monodechlorovancomycin were assayed by HPLC or total microbiological activity was assessed by cylinder plate analysis. The below tables depict stability of the powder at the various conditions.

| Vancomycin Hydrochloride Powder-25° C./60% RH | | | | |
| Time (Months) | Vancomycin | Vancomycin B | Other Impurities | Monodechlorovancomycin |
| --- | --- | --- | --- | --- |
| 0 | 1,112 mcg/mg | 94.7% | <5.0% for all other | 1.5% |
| 3 | 1,070 mcg/mg | 91.8% | <5.0% for all other | 1.1% |

| Vancomycin Hydrochloride Powder-40° C./60% RH | | | | |
| Time (Months) | Vancomycin | Vancomycin B | Other Impurities | Monodechlorovancomycin |
| --- | --- | --- | --- | --- |
| 0 | 1,112 mcg/mg | 94.7% | <5.0% for all other | 1.5% |
| 1 | 1,095 mcg/mg | 91.3% | <5.0% for all other | 1.4% |
| 2 | 1,108 mcg/mg | 90.8% | <5.0% for all other | 1.1% |
| 3 | 1,095 mcg/mg | 87.6% | <5.0% for all other | 1.0% |

Vancomycin hydrochloride powder remained stable through 3 months under accelerated stability conditions and 3 months under ambient (25±2° C./60±5% RH) with slight decrease in the levels of vancomycin B. However, none of the other impurities exceeded 5.0% nor did the Monodechlorovancomycin exceed 4.7%. Stability at ambient conditions was also examined for three additional lots of vancomycin hydrochloride powder at lower concentrations/smaller bottle sizes. Similar results were observed for the levels of vancomycin B.

Reconstituted Liquid Stability: Vancomycin hydrochloride powder was reconstituted in 325 mL bottles according to mixing method (30 seconds of shaking) and stored at refrigerated and ambient 25±2° C./60±5% RH conditions. Aliquots were taken during selected time points during the study period. The below tables depict stability of the reconstituted liquid at various conditions.

| | % vancomycin | |
| | Vancomycin Oral Liquid | |
| Time (Days) | Refrigerated | 25° C./60% (RH) |
| --- | --- | --- |
| 0 | 103.2% | 102.9% |
| 7 | 103.7% | 102.9% |
| 14 | 104.3% | 104.2% |
| 21 | 107.2% | 106.4% |
| 30 | 108.6% | 106.1% |

| | pH | |
| | Vancomycin Oral Liquid | |
| Time (Days) | Refrigerated | 25° C. /60% (RH) |
| --- | --- | --- |
| 0 | 3.0 | 3.0 |
| 7 | 2.8 | 2.8 |
| 14 | 2.9 | 3.0 |
| 21 | 3.1 | 3.2 |
| 30 | 3.0 | 3.2 |

After being reconstituted, the vancomycin oral liquid was stable at refrigerated and ambient conditions with essentially unchanged values of its attributes up to the end of the study period (30 days).

The solution component is tested for description, pH, density, sodium benzoate assay, container/closure, and microbial limits. This testing was also performed at specified stability intervals. All testing reflects unchanged values of attributes up to the end of shelf life.

Example 5: Antimicrobial Effectiveness Testing Stability

Vancomycin hydrochloride powder was reconstituted in 325 mL bottles according to mixing method (30 seconds of shaking) and stored at refrigerated and ambient 25±2° C./60±5% RH conditions. Aliquots were taken during selected time points during the study period. The below tables depicts the antimicrobial effectiveness testing.

| Vancomycin Oral Liquid | | | | | | | |
|---|---|---|---|---|---|---|---|
| | | Test Organism | Initial Inoculum | CFU/ml 14 day | % red* 14 day | CFU/ml 28 day | % red* 28 day |
| Time 0 | 25° C./60% (RH) | E. coli | $4.9 \times 10^5$ | <10 | >99.99 | <10 | >99.99 |
| | | C. albicans | $4.1 \times 10^5$ | <10 | >99.99 | <10 | >99.99 |
| | | A. brasiliensis | $2.6 \times 10^5$ | <10 | >99.99 | <10 | >99.99 |
| Time 7 day | 25° C./60% (RH) | E. coli | $5.8 \times 10^5$ | <10 | >99.99 | <10 | >99.99 |
| | | C. albicans | $3.9 \times 10^5$ | <10 | >99.99 | <10 | >99.99 |
| | | A. brasiliensis | $3.5 \times 10^5$ | <10 | >99.99 | <10 | >99.99 |
| Time 14 day | 25° C./60% (RH) | E. coli | $4.5 \times 10^5$ | <10 | >99.99 | <10 | >99.99 |
| | | C. albicans | $2.9 \times 10^5$ | <10 | >99.99 | <10 | >99.99 |
| | | A. brasiliensis | $3.8 \times 10^5$ | <10 | >99.99 | <10 | >99.99 |
| Time 30 day | 25° C./60% (RH) | E. coli | $4.6 \times 10^5$ | <10 | >99.99 | <10 | >99.99 |
| | | C. albicans | $3.6 \times 10^5$ | <10 | >99.99 | <10 | >99.99 |
| | | A. brasiliensis | $3.9 \times 10^5$ | <10 | >99.99 | <10 | >99.99 |

*% reduction

| Vancomycin Oral Liquid | | | | | | | |
|---|---|---|---|---|---|---|---|
| | | Test Organism | Initial Inoculum | CFU/ml 14 day | % red* 14 day | CFU/ml 28 day | % red* 28 day |
| Time 0 | Refrigerated | E. coli | $4.9 \times 10^5$ | <10 | >99.99 | <10 | >99.99 |
| | | C. albicans | $4.1 \times 10^5$ | <10 | >99.99 | <10 | >99.99 |
| | | A. brasiliensis | $2.6 \times 10^5$ | $1.2 \times 10^3$ | 99.54 | $1.3 \times 10^2$ | 99.95 |
| Time 7 day | Refrigerated | E. coli | $5.8 \times 10^5$ | <10 | >99.99 | <10 | >99.99 |
| | | C. albicans | $3.9 \times 10^5$ | <10 | >99.99 | <10 | >99.99 |
| | | A. brasiliensis | $3.5 \times 10^5$ | $2.3 \times 10^3$ | 99.34 | $3.1 \times 10^2$ | 99.91 |
| Time 14 day | Refrigerated | E. coli | $4.5 \times 10^5$ | <10 | >99.99 | <10 | >99.99 |
| | | C. albicans | $2.9 \times 10^5$ | <10 | >99.99 | <10 | >99.99 |
| | | A. brasiliensis | $3.8 \times 10^5$ | $2.9 \times 10^3$ | 99.24 | $5.0 \times 10^1$ | 99.99 |
| Time 30 day | Refrigerated | E. coli | $4.6 \times 10^5$ | <10 | >99.99 | <10 | >99.99 |
| | | C. albicans | $3.6 \times 10^5$ | $1.0 \times 10^1$ | >99.99 | <10 | >99.99 |
| | | A. brasiliensis | $3.9 \times 10^5$ | $1.1 \times 10^3$ | 99.72 | <10 | >99.99 |

*% reduction

Example 6: Antimicrobial Effectiveness Testing Stability for Extemporaneous Compounding The most common extemporaneous compounding method for vancomycin oral liquid is to reconstitute lyophilized vancomycin HCL powder for injection with sterile water. Lyophilized vancomycin hydrochloride powder for injection was reconstituted in 325 mL bottles and stored at refrigerated and ambient 25±2° C./60±5% RH conditions. Aliquots were taken during selected time points during the study period. The below tables depicts the antimicrobial effectiveness testing. The test requirement is to assure no growth in either yeast or mold is observed throughout the inoculation. The extemporaneous compounding method fails to meet these criteria. If contamination were to occur the extemporaneous compounding method does not preserve against mold or yeast.

| Vancomycin Oral Liquid | | | | | | | |
|---|---|---|---|---|---|---|---|
| | | Test Organism | Initial Inoculum | CFU/ml 14 day | % red* 14 day | CFU/ml 28 day | % red* 28 day |
| Time 0 | 25° C./60% (RH) | E. coli | $4.9 \times 10^5$ | <10 | >99.99 | <10 | >99.99 |
| | | C. albicans | $4.1 \times 10^5$ | $1.9 \times 10^3$ | 99.54 | $1.8 \times 10^3$ | 99.56 |
| | | A. brasiliensis | $2.6 \times 10^5$ | $2.8 \times 10^5$ | 0** | $8.0 \times 10^4$ | 69.23 |
| Time 7 day | 25° C./60% (RH) | E. coli | $5.8 \times 10^5$ | <10 | >99.99 | <10 | >99.99 |
| | | C. albicans | $3.9 \times 10^5$ | $5.2 \times 10^3$ | 98.67 | $1.65 \times 10^3$ | 99.58 |
| | | A. brasiliensis | $3.5 \times 10^5$ | $3.6 \times 10^5$ | 0** | $3.2 \times 10^5$ | 8.57 |
| Time 14 day | 25° C./60% (RH) | E. coli | $4.5 \times 10^5$ | <10 | >99.99 | <10 | >99.99 |
| | | C. albicans | $2.9 \times 10^5$ | $4.1 \times 10^3$ | 98.59 | $4.0 \times 10^3$ | 98.62 |
| | | A. brasiliensis | $3.8 \times 10^5$ | $2.7 \times 10^5$ | 28.95 | $2.5 \times 10^5$ | 34.21 |
| Time 30 day | 25° C./60% (RH) | E. coli | $4.6 \times 10^5$ | <10 | >99.99 | <10 | >99.99 |
| | | C. albicans | $3.6 \times 10^5$ | $8.2 \times 10^4$ | 77.22 | $3.5 \times 10^4$ | 90.28 |
| | | A. brasiliensis | $3.9 \times 10^5$ | $2.9 \times 10^5$ | 25.64 | $1.8 \times 10^5$ | 53.85 |

| | | | Vancomycin Oral Liquid | | | | |
|---|---|---|---|---|---|---|---|
| | | Test Organism | Initial Inoculum | CFU/ml 14 day | % red* 14 day | CFU/ml 28 day | % red* 28 day |
| Time 0 | Refrigerated | E. coli | $4.9 \times 10^5$ | <10 | >99.99 | <10 | >99.99 |
| | | C. albicans | $4.1 \times 10^5$ | $9.7 \times 10^3$ | 97.63 | $8.6 \times 10^3$ | 97.90 |
| | | A. brasiliensis | $2.6 \times 10^5$ | $3.2 \times 10^5$ | 0** | $1.6 \times 10^5$ | 38.46 |
| Time 7 day | Refrigerated | E. coli | $5.8 \times 10^5$ | <10 | >99.99 | <10 | >99.99 |
| | | C. albicans | $3.9 \times 10^5$ | $6.5 \times 10^4$ | 83.33 | $8.2 \times 10^4$ | 78.97 |
| | | A. brasiliensis | $3.5 \times 10^5$ | $3.8 \times 10^5$ | 0** | $3.0 \times 10^5$ | 14.29 |
| Time 14 day | Refrigerated | E. coli | $4.5 \times 10^5$ | <10 | >99.99 | <10 | >99.99 |
| | | C. albicans | $2.9 \times 10^5$ | $1.5 \times 10^4$ | 94.79 | <10 | >99.99 |
| | | A. brasiliensis | $3.8 \times 10^5$ | $2.6 \times 10^5$ | 31.58 | $2.0 \times 10^5$ | 47.37 |
| Time 30 day | Refrigerated | E. coli | $4.6 \times 10^5$ | <10 | >99.99 | <10 | >99.99 |
| | | C. albicans | $3.6 \times 10^5$ | $1.3 \times 10^4$ | 96.39 | $1.0 \times 10^2$ | 99.97 |
| | | A. brasiliensis | $3.9 \times 10^5$ | $2.6 \times 10^5$ | 33.33 | $1.7 \times 10^5$ | 56.41 |

*% reduction
**Fails criteria Category 3 (yeast and mold): no increase from the initial calculated count at 14 and 28 days.

Example 7: Long Term Stability Analysis

The stability of the vancomycin hydrochloride solution of the invention was compared directly to the stability of a vancomycin hydrochloride solution made from a sterile lyophilized powder typically used for making an injectable solution. The results are shown in the following Table.

| | Solution Using Sterile Lyophilized Powder Vancomycin HCl 145 mL of sterile water for injection (50 mg/mL solution) | | | Solution of the Invention Vancomycin HCl 145 mL liquid formulation (50 mg/ML solution) | | |
|---|---|---|---|---|---|---|
| Days | Appearance | pH | Precipitate | Appearance Amber | pH | Precipitate |
| Time 0 | Light tan color | 3.23 | 1 | | 3.2 | 1 |
| 1 | | | | Amber | | |
| 2 | Light tan color | | | Amber | | |
| 3 | Light tan color | 3.2 | 1 | | 3.2 | 1 |
| 4 | | 3.2 | 1 | | 3.1 | 1 |
| 5 | | | | Amber | | |
| 6 | Light tan color | | | Amber | | |
| 7 | Light tan color | 3.2 | 1 | | 3 | 1 |
| 8 | | 3.2 | 1 | | 3.1 | 1 |
| 9 | | | | Amber | | |
| 10 | Light tan color | | | | | |
| 11 | | 3.2 | 1 | | 3 | 1 |
| 12 | | | | Amber | | |
| 13 | Light tan color | | | Amber | | |
| 14 | Light tan color | 3.2 | 1 | Amber | 3 | 1 |
| 15 | Light tan color | 3.2 | 1 | Amber | 3.2 | 1 |
| 16 | Light tan color | 3.2 | 1 | Amber | 3.1 | 1 |
| 17 | Light tan color | 3.2 | 1 | | 3.1 | 1 |
| 18 | | 3.2 | 1 | | 3.1 | 1 |
| 19 | | | | Amber | | |
| 20 | Light tan color | | | Amber | | |
| 21 | Light tan color | 3.2 | 1 | Amber | 3.1 | 1 |
| 22 | Light tan color | 3.2 | 1 | Amber | 3.2 | 1 |
| 23 | Light tan color | 3.2 | 1 | Amber | 3.2 | 1 |
| 24 | Light tan color | 3.2 | 1 | | 3.1 | 1 |
| 25 | | 3.2 | 1 | | 3.2 | 1 |
| 26 | | | | Amber | | |
| 27 | Light tan color | | | Amber | | |
| 28 | Light tan color | 3.2 | 1 | Amber | 3.1 | 1 |
| 29 | Light tan color | 3.2 | 1 | Amber | 3.1 | 1 |
| 30 | Light tan color | 3.2 | 1 | Amber | 3.1 | 1 |
| 31 | Light tan color | 3.2 | 1 | | 3.2 | 1 |
| 32 | | 3.2 | 1 | | 3.2 | 1 |
| 33 | | | | Amber | | |
| 34 | Light tan color | | | Amber | | |
| 35 | Light tan color | 3.2 | 1 | Amber | 3.1 | 1 |
| 36 | Light tan color | 3.2 | 1 | Amber | 3.1 | 1 |
| 37 | Light tan color | 3.2 | 1 | Amber | 3.1 | 1 |
| 38 | Light tan color | 3.2 | 1 | | 3.2 | 1 |
| 39 | | 3.2 | 1 | | 3.2 | 1 |
| 40 | | | | Amber | | |
| 41 | Light tan color | | | Amber | | |
| 42 | Light tan color | 3.2 | 1 | | 3.2 | 1 |
| 43 | Out | 3.2 | 2 | Amber | 3.2 | 1 |
| 44 | Light tan color | | | Amber | | |
| 45 | Light tan color | 3.2 | 2 | | 3.2 | 1 |
| 46 | | 3.2 | 3 | | 3.2 | 1 |
| 47 | | | | Amber | | |
| 48 | Light tan color | | | Amber | | |
| 49 | Taken for analysis | 3.2 | 4 | Amber | 3.2 | 1 |
| 50 | | 3.2 | 4 | Amber | 3.2 | 1 |
| 51 | | | | | 3.2 | 1 |
| 52 | | | | | 3.2 | 1 |
| 53 | | | | | | |
| 54 | | | | | | |
| 55 | Holiday | | | | | |
| 56 | Out | | | Amber | | |
| 57 | | | | Amber | | |
| 58 | | | | Amber | 3.2 | 2 |
| 59 | | | | | 3.2 | 3 |
| 60 | | | | | 3.2 | 4 |

1 = Free of particles
2 = Small amount of particles visible
3 = Large amount of particles visible
4 = Completely out of solution At day 43 for the vancomycin solution with lyophilized powder small amounts of particles were visible. At day 49 the particles were abundant and were observed to be completely out of solution.

In contrast, the solution of the invention was particle free through at least day 58, when a small amount of particles were visible. It remained in solution through day 60.

Example 8: Long Term Stability Analysis of Three Different Preparations of Vancomycin Stored at Ambient and Refrigerated Temperatures for Up to 30 Days The stability of the vancomycin hydrochloride solution of the invention was compared directly to the stability of a vancomycin hydrochloride solution made from a sterile lyophilized powder typically used for making an injectable solution and vancomycin capsules ground to a powder and reconstituted. To determine the impact of storage on the potency of vancomycin, the different formulations were tested at the time of preparation, after 14 and 30 days, stored at ambient and refrigerator temperatures by measuring MICs for 25 strains of C. difficile. The control was vancomycin reference standard powder that had been reconstituted to prepare a stock solution, then stored at −70 C. The vancomycin hydrochloride solution of the invention and the IV solution were reconstituted to a concentration of 25 mg/ml. The generic "capsules" were tablets that had to be ground to a fine powder before they would dissolve in water. The MICs were determined by the reference agar dilution method (CLSI M11-A8). All serial two-fold dilutions were prepared on the same day and added to molten agar to prepare plates.

The following materials were used in the study:
Vancomycin from Cutis Pharma Inc. Lot E836 reconstituted to 25 mg/ml
Vancomycin for IV reconstituted to 25 mg/ml Hospira Inc. Lot 322578E04
Vancomycin capsules Prasco Lot 453019, ground to a powder and reconstituted to 25 mg/ml
Vancomycin laboratory standard powder, Sigma, Lot SLBD44270 Brucella deeps, Anaerobe Systems (Morgan Hill, Calif.) Lot 3551809
Hemostat Sheep blood Lot 199032-15
Brucella blood agar plates, Hardy Diagnostics (Santa Maria, Calif.) Lot 14064

The in vitro activity was tested for three different preparations of vancomycin freshly reconstituted, and stored at ambient and at refrigerated temperatures. The C. difficile strains were selected to represent the most frequently encountered ribotypes. MICs for the preparations were measured by agar dilution according to the procedures in the CSI M11-A8 document (Clinical and Laboratory Standards Institute. 2012. Methods for antimicrobial susceptibility testing of anaerobic bacteria; approved standard-eighth edition. CLSI document M11-A8. CLSI, Wayne, Pa.). Quality control strains included Clostridium difficile ATCC 700057 and Staphylococcus aureus ATCC 29213.

The organisms were recovered from clinical samples, identified by standard methods (Jousimies-Somer, H. R., et al 2002. Wadsworth-KTL Anaerobic Bacteriology Manual. Star Publishing, Belmont, Calif.) and stored in 20% skim milk at −70° C. They were taken from the freezer and subcultured at least twice on supplemented Brucella agar and incubated under anaerobic conditions at 37° C. for 24 h prior to testing. Inocula were prepared by direct suspensions of colonies into Brucella broth to equal the turbidity of the 0.5 McFarland standard.

Plates were prepared by adding 1 ml of lysed sheep blood and two mls of the twofold dilutions of the vancomycin preparations to molten agar. Plates were mixed, poured and allowed to harden. Suspensions of the organisms were applied to the plates using a Steers replicating device that delivered approximately $10^5$ cfu/spot. Each preparation was tested in triplicate. Plates were incubated at 37° C. for 48 h.

Plates were examined for growth. The MIC was defined as the concentration that completely inhibited growth or caused a major reduction in the appearance of the button compared to the drug-free control plate.

The results are shown in the following Tables. Table 1 presents the results as the most frequent of the triplicates. Table 2 presents the average of the three MICs.

Figure 2:
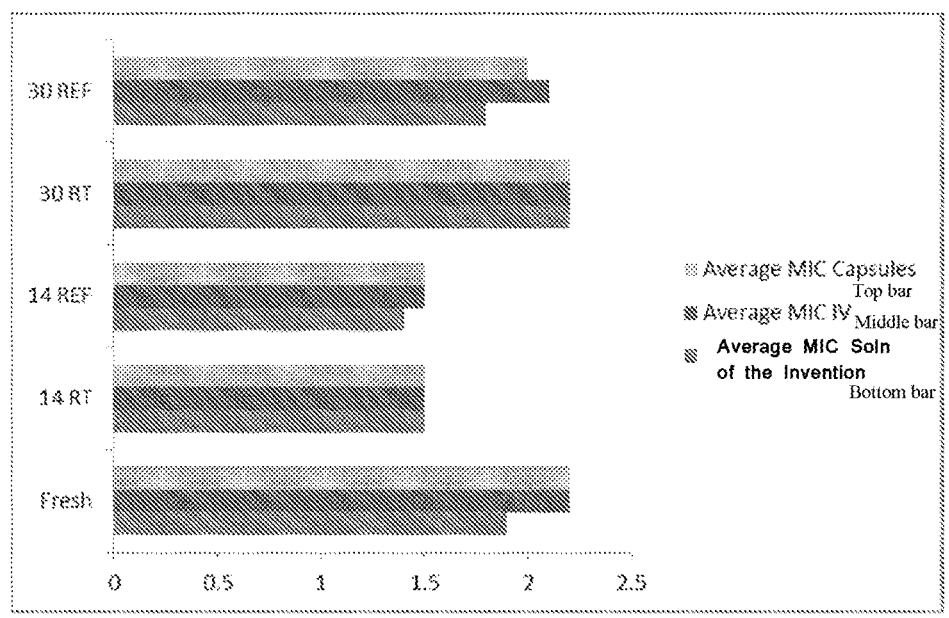
FIG. 2 is a bar graph depicting average MIC values for three formulations over a 30 day testing period.

The triplicate MICs (μg/ml) were averaged for each organism and the geometric mean was calculated for all 25 strains, preparations and time periods. The MICs for each preparation at T(0), 14 d and 30 d at ambient/refrigerator were as follows: vancomycin solution of the invention 1.9, 1.5/1.4, 2.2/1.8; IV solution 2.2,1.5/1.5, 2.2/2.1; crushed tablets 2.2, 1.5/1.5, 2.3/2.0, respectively. The reference method was 1.5 μg/ml. The differences were less than one dilution for all of the values and were considered insignificant. MICs showed minimal variation among all preparations over the study period. However, the average MICs of the vancomycin solution of the invention were shown to be lower than the other preparations in several instances, as shown in Table 3 below and FIG. 2. FIG. 2 is a Bar graph showing the average MIC values for each of the solutions at each of the time points. Vancomycin was remarkably stable in the preparations, regardless of storage conditions, for up to 30 days.

TABLE 1

C. difficile vancomycin MICs from triplicate test. Results shown as the best of 3 values

| | | Solution of the Invention | | | | | IV | | | | |
|---|---|---|---|---|---|---|---|---|---|---|---|
| | | | 14 d | | 30 d | | | 14 d | | 30 d | |
| RMA# | RIBOTYPE | Fresh | RT | REFRIG | RT | REFRIG | Fresh | RT | REFRIG | RT | REFRIG |
| 24608 | 002 | 2 | 1 | 1 | 2 | 2 | 2 | 1 | 1 | 2 | 2 |
| 24605 | 002 | 2 | 1 | 1 | 2 | 2 | 2 | 1 | 1 | 2 | 2 |
| 24655 | 005 | 2 | 1 | 1 | 2 | 2 | 2 | 2 | 2 | 2 | 2 |
| 24615 | 005 | 2 | 2 | 2 | 2 | 2 | 2 | 2 | 2 | 4 | 2 |
| 24678 | 012 | 4 | 4 | 4 | 4 | 4 | 4 | 4 | 4 | 4 | 4 |
| 24628 | 012 | 2 | 1 | 1 | 2 | 2 | 2 | 1 | 1 | 2 | 2 |
| 24527 | 014 | 1 | 1 | 1 | 2 | 1 | 2 | 1 | 1 | 2 | 2 |
| 24529 | 014 | 1 | 1 | 1 | 2 | 1 | 2 | 1 | 1 | 2 | 1 |
| 24547 | 014 | 2 | 1 | 1 | 2 | 2 | 2 | 1 | 1 | 2 | 2 |
| 24541 | 020 | 1 | 1 | 1 | 2 | 1 | 2 | 1 | 1 | 2 | 2 |
| 24543 | 020 | 1 | 1 | 1 | 2 | 1 | 2 | 1 | 1 | 2 | 2 |
| 24567 | 020 | 2 | 1 | 1 | 2 | 2 | 2 | 1 | 2 | 2 | 2 |
| 24504 | 027 | 2 | 1 | 1 | 2 | 1 | 2 | 1 | 1 | 2 | 2 |
| 24510 | 027 | 2 | 1 | 1 | 2 | 1 | 2 | 1 | 1 | 2 | 2 |

TABLE 1-continued

*C. difficile* vancomycin MICs from triplicate test. Results shown as the best of 3 values

| RMA# | Ribotype | | | | | | | | | | |
|---|---|---|---|---|---|---|---|---|---|---|---|
| 24519 | 027 | 1 | 1 | 1 | 2 | 1 | 1 | 1 | 1 | 2 | 2 |
| 24683 | 027 | 2 | 2 | 2 | 2 | 1 | 2 | 2 | 2 | 2 | 2 |
| 24690 | 027 | 4 | 4 | 4 | 4 | 4 | 4 | 4 | 4 | 4 | 4 |
| 24561 | 078 | 1 | 1 | 1 | 1 | 1 | 1 | 1 | 1 | 1 | 1 |
| 24575 | 078 | 1 | 1 | 1 | 2 | 1 | 1 | 1 | 1 | 2 | 1 |
| 24601 | 106 | 2 | 1 | 1 | 2 | 2 | 2 | 2 | 1 | 2 | 2 |
| 24607 | 106 | 2 | 1 | 1 | 2 | 2 | 2 | 1 | 1 | 2 | 2 |
| 24594 | 106 | 4 | 4 | 4 | 4 | 4 | 4 | 4 | 4 | 4 | 4 |
| 24641 | 001/072 | 2 | 1 | 1 | 2 | 2 | 2 | 1 | 1 | 2 | 2 |
| 24643 | 001/072 | 2 | 1 | 1 | 2 | 2 | 2 | 1 | 1 | 2 | 2 |
| 24646 | 001/072 | 2 | 1 | 1 | 2 | 2 | 2 | 1 | 1 | 2 | 2 |
| ATCC | 7000057 QC | 2 | 1 | 1 | 2 | 2 | 2 | 2 | 2 | 2 | 2 |
| ATCC | 29213 SA QC | | 2 | 1 | | | | 2 | 2 | | |

| RMA# | | Capsules Fresh | 14 D RT | 14 D REFRIG | 30 D RT | 30 D REFRIG | Reference standard Fresh | |
|---|---|---|---|---|---|---|---|---|
| 24608 | 002 | 2 | 1 | 1 | 2 | 2 | 1 | |
| 24605 | 002 | 2 | 1 | 1 | 2 | 2 | 1 | |
| 24655 | 005 | 2 | 2 | 1 | 2 | 2 | 2 | |
| 24615 | 005 | 2 | 2 | 2 | 2 | 2 | 2 | |
| 24678 | 012 | 4 | 4 | 4 | 4 | 4 | 4 | |
| 24628 | 012 | 2 | 1 | 1 | 2 | 2 | 1 | |
| 24527 | 014 | 2 | 1 | 1 | 2 | 1 | 1 | |
| 24529 | 014 | 2 | 1 | 1 | 2 | 1 | 1 | |
| 24547 | 014 | 2 | 1 | 1 | 2 | 1 | 1 | |
| 24541 | 020 | 2 | 1 | 1 | 2 | 2 | 1 | |
| 24543 | 020 | 2 | 1 | 1 | 2 | 2 | 1 | |
| 24567 | 020 | 2 | 1 | 1 | 2 | 2 | 1 | |
| 24504 | 027 | 2 | 1 | 1 | 2 | 2 | 1 | |
| 24510 | 027 | 2 | 1 | 1 | 2 | 2 | 1 | |
| 24519 | 027 | 2 | 1 | 1 | 2 | 1 | 1 | |
| 24683 | 027 | 2 | 2 | 2 | 2 | 2 | 2 | |
| 24690 | 027 | 4 | 4 | 4 | 4 | 4 | 4 | |
| 24561 | 078 | 1 | 1 | 1 | 1 | 1 | 1 | |
| 24575 | 078 | 1 | 1 | 1 | 2 | 1 | 1 | |
| 24601 | 106 | 2 | 2 | 1 | 2 | 2 | 2 | |
| 24607 | 106 | 2 | 1 | 1 | 2 | 2 | 1 | |
| 24594 | 106 | 4 | 4 | 4 | 4 | 4 | 4 | |
| 24641 | 001/072 | 2 | 1 | 1 | 2 | 2 | 1 | |
| 24643 | 001/072 | 2 | 1 | 1 | 2 | 2 | 1 | |
| 24646 | 001/072 | 2 | 1 | 1 | 2 | 2 | 1 | |
| ATCC | 7000057 QC | 2 | 2 | 1 | 2 | 2 | 1 | *C. difficile* |
| ATCC | 29213 SA CQ | | 2 | 1 | | | 2 | *S. aureus* |

TABLE 2

*C. difficile* Vancomycin susceptibilities - average of triplicate MIC values

| | | Solution of the Invention | | | | | IV | | | | |
|---|---|---|---|---|---|---|---|---|---|---|---|
| | | | 14 d | | 30 d | | | 14 d | | 30 d | |
| RMA# | RIBOTYPE | Fresh | RT | REFRIG | RT | REFRIG | Fresh | RT | REFRIG | RT | REFRIG |
| 24608 | 002 | 2 | 1 | 1 | 2 | 2 | 2 | 1 | 1 | 2 | 2 |
| 24605 | 002 | 2 | 1 | 1 | 2 | 2 | 2 | 1 | 1 | 2 | 2 |
| 24655 | 005 | 1.7 | 1.3 | 1.3 | 2 | 2 | 2 | 1.7 | 2 | 2 | 2 |
| 24615 | 005 | 2 | 2 | 1.7 | 2 | 2 | 2.7 | 2 | 2 | 3.3 | 2 |
| 24678 | 012 | 4 | 4 | 4 | 4 | 4 | 4 | 4 | 4 | 4 | 4 |
| 24628 | 012 | 2 | 1 | 1 | 2 | 2 | 2.7 | 1 | 1 | 2 | 2 |
| 24527 | 014 | 1 | 1 | 1 | 2 | 1 | 1.7 | 1 | 1 | 2 | 1.7 |
| 24529 | 014 | 1 | 1 | 1 | 2 | 1 | 1.7 | 1 | 1 | 2 | 1.3 |
| 24547 | 014 | 2 | 1 | 1 | 2 | 2 | 2 | 1 | 1 | 2 | 2 |
| 24541 | 020 | 1.3 | 1 | 1 | 2 | 1 | 2 | 1 | 1 | 2 | 1.7 |
| 24543 | 020 | 1 | 1 | 1 | 2 | 1 | 2.7 | 1 | 1 | 2 | 1.7 |
| 24567 | 020 | 2 | 1 | 1 | 2 | 2 | 2 | 1 | 1.7 | 2 | 2 |
| 24504 | 027 | 1.7 | 1 | 1 | 2 | 1 | 2 | 1 | 1 | 2 | 2 |
| 24510 | 027 | 1.7 | 1 | 1 | 2 | 1 | 2 | 1 | 1 | 2 | 2 |
| 24519 | 027 | 1 | 1 | 1 | 2 | 1 | 1.3 | 1 | 1 | 2 | 1.7 |
| 24683 | 027 | 1.7 | 2 | 2 | 2 | 1 | 2 | 2 | 2 | 2 | 2 |
| 24690 | 027 | 4 | 4 | 4 | 4 | 4 | 4 | 4 | 4 | 4 | 4 |
| 24561 | 078 | 1 | 1 | 1 | 1 | 1 | 1 | 1 | 1 | 1 | 1 |
| 24575 | 078 | 1 | 1 | 1 | 2 | 1 | 1.3 | 1 | 1 | 1.7 | 1 |

TABLE 2-continued

C. difficile Vancomycin susceptibilities - average of triplicate MIC values

| | | | | | | | | | | | |
|---|---|---|---|---|---|---|---|---|---|---|---|
| 24601 | 106 | 2 | 1 | 1 | 2 | 2 | 2 | 1.7 | 1 | 2 | 2 |
| 24607 | 106 | 2 | 1 | 1 | 2 | 2 | 2 | 1 | 1 | 2 | 2 |
| 24594 | 106001/07 | 4 | 4 | 4 | 4 | 4 | 4 | 4 | 4 | 4 | 4 |
| 24641 | 200/107 | 2 | 1 | 1 | 2 | 2 | 2 | 1 | 1 | 2 | 2 |
| 24643 | 2001/07 | 2 | 1 | 1 | 2 | 2 | 2 | 1 | 1 | 2 | 2 |
| 24646 | 2 | 2 | 1 | 1 | 2 | 2 | 2 | 1 | 1.3 | 2 | 2 |
| ATCC | 7000057 QC | 2 | 1 | 1 | 2 | 2 | 2 | 1.7 | 1.7 | 2 | 2 |
| ATCC | 29213 SA QC | | 2 | 1.3 | | | | 2 | 2 | | |

| | | Capsules | | | | Reference | |
|---|---|---|---|---|---|---|---|
| | | 14 d | | 30 d | | Standard | |
| RMA# | RIBOTYPE | Fresh | RT | REFRIG | RT | REFRIG | Fresh |
| 24608 | 002 | 2 | 1 | 1 | 2 | 2 | 1 |
| 24605 | 002 | 2 | 1 | 1 | 2 | 2 | 1 |
| 24655 | 005 | 2 | 2 | 1.3 | 2 | 2 | 2 |
| 24615 | 005 | 2.7 | 2.7 | 2 | 2.7 | 2 | 2 |
| 24678 | 012 | 4 | 4 | 4 | 4 | 4 | 4 |
| 24628 | 012 | 2 | 1 | 1 | 2 | 2 | 1 |
| 24527 | 014 | 1.7 | 1 | 1 | 2 | 1.3 | 1 |
| 24529 | 014 | 2 | 1 | 1 | 2 | 1.3 | 1 |
| 24547 | 014 | 2 | 1 | 1 | 2 | 1 | 1 |
| 24541 | 020 | 1.7 | 1 | 1 | 2 | 1.7 | 1 |
| 24543 | 020 | 1.7 | 1 | 1 | 2 | 1.7 | 1 |
| 24567 | 020 | 2 | 1 | 1 | 2 | 1.7 | 1 |
| 24504 | 027 | 2 | 1 | 1 | 2 | 2 | 1 |
| 24510 | 027 | 2 | 1 | 1 | 2 | 2 | 1 |
| 24519 | 027 | 2 | 1 | 1 | 2 | 1.3 | 1 |
| 24683 | 027 | 2 | 2 | 2 | 2 | 1.7 | 2 |
| 24690 | 027 | 4 | 4 | 4 | 4 | 4 | 4 |
| 24561 | 078 | 1 | 1 | 1 | 1 | 1 | 1 |
| 24575 | 078 | 1.3 | 1 | 1 | 2 | 1 | 1 |
| 24601 | 106 | 2 | 1.7 | 1 | 1.7 | 2 | 2 |
| 24607 | 106 | 2 | 1 | 1 | 2 | 2 | 1 |
| 24594 | 106001/07 | 4 | 4 | 4 | 4 | 4 | 4 |
| 24641 | 2001/07 | 2 | 1 | 1 | 2 | 2 | 1 |
| 24643 | 2001/07 | 2 | 1 | 1 | 2 | 2 | 1 |
| 24646 | 2 | 2 | 1 | 1 | 2 | 2 | 1 |
| ATCC | 7000057 QC | 2 | 1.7 | 1.3 | 2 | 2 | 1 | C. difficile |
| ATCC | 29213 SA CQ | | 2 | 1.3 | | | 2 | S. aureus |

TABLE 3

Average MIC

| | Solution of Invention | IV | Capsules |
|---|---|---|---|
| Fresh | 1.9 | 2.2 | 2.2 |
| 14 RT | 1.5 | 1.5 | 1.5 |
| 14 REF | 1.4 | 1.5 | 1.5 |
| 30 RT | 2.2 | 2.2 | 2.2 |
| 30 REF | 1.8 | 2.1 | 2 |

Example 9: In Vitro Study of the Activity of Two Different Preparations of Vancomycin (Sigma, Cutis) Against *Clostridium difficile* with Known Ribotypes Introduction: The purpose of the study was to compare the MICs obtained with the formulation of vancomycin HCL of the invention (Cutis) to formulations obtained using a vancomycin HCL reference standard powder obtained from Sigma. The Example also involves the analysis of a solution or diluent to determine if it has antimicrobial activity at the concentrations present in the agar dilution test.

Materials
*Brucella* agar deeps—Anaerobe systems, Lot 3021809
Vancomycin HCl, Sigma, Lot SLBG4650V
Vancomycin, Cutis, Lot E951
Na citrate, Baker, Lot 423343
Na benzoate, Emerald, Lot KASBD46212
Methods:

The *C. difficile* were tested by agar dilution according to the procedures in the Clinical and Laboratory Standards Institute. 2012. Methods for antimicrobial susceptibility testing of anaerobic bacteria; approved standard-seventh edition.

Other anaerobic organisms included clinical isolates of *Bifidobacterium adolescentis* and *Bacteroides fragilis*. *Clostridium difficile* ATCC 700057 was included as a quality control strain.

The *C. difficile* isolates were recovered from patients with CDI during the past two years and stored at −70° C. in 20% skim milk. Ribotyping was performed by another reference laboratory. The strains were taken from the freezer and subcultured at least twice to ensure purity and good growth.

On the day of testing, they were suspended in *Brucella* broth to the turbidity of the 0.5 McFarland standard for testing.

Stock solution of the Sigma vancomycin was prepared in water and stored at −70° C. On the day of testing, it was thawed and further diluted in water to obtain the desired range of 16-0.125 µg/ml. The Cutis vancomycin (25 mg/ml) was reconstituted on the day of testing and further diluted for a final range of 16-0.125 µg/ml in the test. The antimicrobials were added to molten *Brucella* agar supplemented with vitamin K and hemin to prepare the plates. Drug-free growth controls were included for testing before and after each set of plates. All testing was done in triplicate.

The organisms were pipetted into the wells of the Steers replicator head and applied to the plates with the multi-pronged replicator. The final concentration of organisms was ~$10^5$ CFU/spot.

The plates were incubated in the anaerobic chamber incubator for 44 h and examined for growth. The MIC is defined as the concentration of drug that completely inhibits growth or results in a marked reduction of growth compared to the drug-free growth control.

The results for the vancomycin MICs and the Na benzoate, Na citrate, and the Cutis diluent are presented in Tables 4 and 5. The Cutis diluent comprises: water, about 0.12% (w/v) citric acid (anhydrous), 0.2% (w/v) sucralose, about 0.05% (w/v) artificial grape flavor, 0.1% (w/v) sodium benzoate, about 0.0002% (w/v) D&C Yellow No. 10 and about 0.000038% (w/v) FD&C Red No. 40.

Results

TABLE 4

In vitro activity (ug/ml) of different preparations of vancomycin (Sigma, Cutis) against *Clostridium difficile* and other enteric organisms tested by the agar dilution method

| RMA# | organism | Ribotype | Sigma | | | | Cutis | | | |
|---|---|---|---|---|---|---|---|---|---|---|
| | | | S-VAN-1 | S-VAN-2 | S-VAN-3 | AV | C-VAN-1 | C-VAN-2 | C-VAN-3 | AV |
| 24504 | C. difficile | 027 | 2 | 2 | 2 | 2 | 2 | 2 | 2 | 2 |
| 24510 | C. difficile | 027 | 2 | 2 | 1 | 1.7 | 2 | 2 | 2 | 2 |
| 24519 | C. difficile | 027 | 2 | 2 | 1 | 1.7 | 1 | 1 | 2 | 1.3 |
| 24527 | C. difficile | 014 | 2 | 2 | 2 | 2 | 1 | 2 | 1 | 1.3 |
| 24529 | C. difficile | 014 | 2 | 2 | 2 | 2 | 1 | 2 | 1 | 1.3 |
| 24541 | C. difficile | 020 | 1 | 2 | 2 | 1.7 | 2 | 2 | 2 | 2 |
| 24543 | C. difficile | 020 | 1 | 1 | 2 | 1.3 | 1 | 2 | 2 | 1.7 |
| 24547 | C. difficile | 014 | 1 | 1 | 1 | 1 | 2 | 2 | 2 | 2 |
| 24560 | C. difficile | 078 | 2 | 2 | 1 | 1.7 | 2 | 1 | 2 | 1.7 |
| 24561 | C. difficile | 078 | 2 | 2 | 2 | 2 | 1 | 1 | 2 | 1.3 |
| 24567 | C. difficile | 020 | 2 | 2 | 2 | 2 | 2 | 2 | 2 | 2 |
| 24575 | C. difficile | 078 | 2 | 4 | 2 | 2.7 | 1 | 1 | 1 | 1 |
| 24594 | C. difficile | 106 | 4 | 2 | 4 | 3.3 | 4 | 4 | 4 | 4 |
| 24601 | C. difficile | 106 | 2 | 2 | 2 | 2 | 2 | 2 | 2 | 2 |
| 24605 | C. difficile | 002 | 2 | 2 | 2 | 2 | 2 | 2 | 2 | 2 |
| 24607 | C. difficile | 106 | 2 | 2 | 2 | 2 | 2 | 2 | 2 | 2 |
| 24608 | C. difficile | 002 | 2 | 2 | 2 | 2 | 2 | 2 | 2 | 2 |
| 24615 | C. difficile | 005 | 2 | 2 | 2 | 2 | 2 | 2 | 2 | 2 |
| 24628 | C. difficile | 012001/07 | 2 | 2 | 2 | 2 | 2 | 2 | 2 | 2 |
| 24641 | C. difficile | 2001/07 | 2 | 2 | 2 | 2 | 2 | 2 | 2 | 2 |
| 24643 | C. difficile | 2001/07 | 2 | 2 | 2 | 2 | 2 | 2 | 2 | 2 |
| 24646 | C. difficile | 2 | 2 | 2 | 2 | 2 | 2 | 2 | 2 | 2 |
| 24655 | C. difficile | 005 | 2 | 2 | 2 | 2 | 2 | 2 | 4 | 2.7 |
| 24678 | C. difficile | 012 | 4 | 4 | 4 | 4 | 4 | 4 | 4 | 4 |
| 24683 | C. difficile | 027 | 2 | 2 | 2 | 2 | 2 | 2 | 2 | 2 |
| 24690 | C. difficile | 027 | 4 | 4 | 8 | 5.3 | 4 | 4 | 4 | 4 |
| 21317 | Bif. adolescentis | | 1 | 1 | 1 | 10.8 | 1 | 1 | 1 | 1 |
| 21531 | Bif. adolescentis | | 0.5 | 1 | 1 | 3 | 1 | 1 | 1 | 1 |
| 21551 | Bif. adolescentis | | 1 | 1 | 1 | 1 | 1 | 1 | 1 | 1 |
| 21680 | Bif. adolescentis | | 1 | 1 | 1 | 1 | 1 | 1 | 1 | 1 |
| 21703 | Bif. adolescentis | | 1 | 1 | 1 | 1 | 1 | 1 | 1 | 1 |
| ATCC 700057 | | | 2 | 2 | 2 | 2 | 2 | 2 | 2 | 2 |
| 26381 | C. difficile | 017 | 2 | 2 | 1 | 1.7 | 2 | 2 | 2 | 2 |
| 26442 | C. difficile | 017 | 1 | 1 | 1 | 1 | 1 | 1 | 1 | 1 |
| 26443 | C. difficile | 027 | 4 | 4 | 4 | 4 | 4 | 4 | 4 | 4 |
| 26445 | C. difficile | 017 | 2 | 2 | 2 | 2 | 2 | 2 | 2 | 2 |
| 26446 | C. difficile | 027 | 1 | 1 | 1 | 1 | 2 | 1 | 1 | 1.3 |
| 26447 | C. difficile | 001 | 2 | 2 | 2 | 2 | 1 | 2 | 2 | 1.7 |
| 26451 | C. difficile | 001 | 2 | 2 | 1 | 1.7 | 1 | 2 | 1 | 1.3 |
| 26455 | C. difficile | 027 | 1 | 1 | 1 | 1 | 1 | 1 | 1 | 1 |
| 26457 | C. difficile | 027 | 1 | 1 | 1 | 1 | 1 | 1 | 1 | 1 |
| 26461 | C. difficile | 106 | 1 | 2 | 1 | 1.3 | 2 | 1 | 1 | 1.3 |
| 26463 | C. difficile | 002 | 1 | 2 | 1 | 1.3 | 1 | 2 | 1 | 1.3 |
| 26466 | C. difficile | 020 | 2 | 2 | 1 | 1.7 | 1 | 2 | 1 | 1.3 |
| 26467 | C. difficile | 002 | 1 | 2 | 1 | 1.3 | 1 | 2 | 1 | 1.3 |
| 26471 | C. difficile | 001 | 2 | 2 | 2 | 2 | 2 | 2 | 2 | 2 |
| 26472 | C. difficile | 014 | 1 | 1 | 1 | 1 | 1 | 1 | 2 | 1.3 |
| 26480 | C. difficile | 106 | 1 | 1 | 1 | 1 | 2 | 1 | 2 | 1.7 |
| 26484 | C. difficile | 106 | 1 | 1 | 1 | 1 | 2 | 1 | 1 | 1.3 |
| 26485 | C. difficile | 078 | 2 | 1 | 1 | 1.3 | 2 | 1 | 1 | 1.3 |
| 26489 | C. difficile | 176 | 1 | 1 | 1 | 1 | 1 | 1 | 1 | 1 |
| 26494 | C. difficile | 126 | 1 | 2 | 1 | 1.3 | 1 | 2 | 1 | 1.3 |
| 26500 | C. difficile | 014 | 1 | 1 | 1 | 1 | 1 | 2 | 2 | 1.7 |
| 26503 | C. difficile | 014 | 1 | 1 | 1 | 1 | 2 | 1 | 1 | 1.3 |
| 26543 | C. difficile | 078 | 1 | 1 | 1 | 1 | 1 | 1 | 1 | 1 |
| 26544 | C. difficile | 078 | 2 | 2 | 2 | 2 | 2 | 2 | 2 | 2 |

TABLE 4-continued

In vitro activity (ug/ml) of different preparations of vancomycin (Sigma, Cutis) against
*Clostridium difficile* and other enteric organisms tested by the agar dilution method

| | | | Sigma | | | | Cutis | | | |
|---|---|---|---|---|---|---|---|---|---|---|
| RMA# | organism | Ribotype | S-VAN-1 | S-VAN-2 | S-VAN-3 | AV | C-VAN-1 | C-VAN-2 | C-VAN-3 | AV |
| 26563 | *C. difficile* | 018 | 1 | 1 | 1 | 1 | 1 | 1 | 1 | 1 |
| 26572 | *C. difficile* | 017 | 2 | 2 | 1 | 1.7 | 2 | 2 | 1 | 1.7 |
| 26982 | *B. fragilis* | | >16 | >16 | >16 | >16 | >16 | >16 | >16 | >16 |
| 26981 | *B. fragilis* | | >16 | >16 | >16 | >16 | >16 | >16 | >16 | >16 |
| 26980 | *B. fragilis* | | >16 | >16 | >16 | >16 | >16 | >16 | >16 | >16 |
| 26979 | *B. fragilis* | | >16 | >16 | >16 | >16 | >16 | >16 | >16 | >16 |
| 26978 | *B. fragilis* | | >16 | >16 | >16 | >16 | >16 | >16 | >16 | >16 |
| ATCC 700057 | *C. difficile* | | 2 | 2 | 2 | 2 | 2 | 2 | 2 | 2 |

AV, average

TABLE 5

In vitro activity of diluent, Na benzoate and Na citrate, and against
*Clostridium difficile* and other enteric organisms tested by the agar dilution method

| RMA# | organism | Ribotype | diluent 10% | diluent 20% | Na benz 0.02% | Na benz 0.01% | Na benz 0.005% | Na citrate |
|---|---|---|---|---|---|---|---|---|
| 24504 | *C. difficile* | 027 | gr | gr | gr | gr | gr | >0.5% |
| 24510 | *C. difficile* | 027 | gr | gr | gr | gr | gr | >0.5% |
| 24519 | *C. difficile* | 027 | gr | gr | gr | gr | gr | >0.5% |
| 24527 | *C. difficile* | 014 | gr | gr | gr | gr | gr | >0.5% |
| 24529 | *C. difficile* | 014 | gr | gr | gr | gr | gr | >0.5% |
| 24541 | *C. difficile* | 020 | gr | gr | gr | gr | gr | >0.5% |
| 24543 | *C. difficile* | 020 | gr | gr | gr | gr | gr | >0.5% |
| 24547 | *C. difficile* | 014 | gr | gr | gr | gr | gr | >0.5% |
| 24560 | *C. difficile* | 078 | gr | gr | gr | gr | gr | >0.5% |
| 24561 | *C. difficile* | 078 | gr | gr | gr | gr | gr | >0.5% |
| 24567 | *C. difficile* | 020 | gr | gr | gr | gr | gr | >0.5% |
| 24575 | *C. difficile* | 078 | gr | gr | gr | gr | gr | >0.5% |
| 24594 | *C. difficile* | 106 | gr | gr | gr | gr | gr | >0.5% |
| 24601 | *C. difficile* | 106 | gr | gr | gr | gr | gr | >0.5% |
| 24605 | *C. difficile* | 002 | gr | gr | gr | gr | gr | >0.5% |
| 24607 | *C. difficile* | 106 | gr | gr | gr | gr | gr | >0.5% |
| 24608 | *C. difficile* | 002 | gr | gr | gr | gr | gr | >0.5% |
| 24615 | *C. difficile* | 005 | gr | gr | gr | gr | gr | >0.5% |
| 24628 | *C. difficile* | 012 | gr | gr | gr | gr | gr | >0.5% |
| 24641 | *C. difficile* | 001/072 | gr | gr | gr | gr | gr | >0.5% |
| 24643 | *C. difficile* | 001/072 | gr | gr | gr | gr | gr | >0.5% |
| 24646 | *C. difficile* | 001/072 | gr | gr | gr | gr | gr | >0.5% |
| 24655 | *C. difficile* | 005 | gr | gr | gr | gr | gr | >0.5% |
| 24678 | *C. difficile* | 012 | gr | gr | gr | gr | gr | >0.5% |
| 24683 | *C. difficile* | 027 | gr | gr | gr | gr | gr | >0.5% |
| 24690 | *C. difficile* | 027 | gr | gr | gr | gr | gr | >0.5% |
| 700057 | *C. difficile* | QC | gr | gr | gr | gr | gr | >0.5% |
| 26381 | *C. difficile* | 017 | gr | gr | gr | gr | gr | >0.5% |
| 26442 | *C. difficile* | 017 | gr | gr | gr | gr | gr | >0.5% |
| 26443 | *C. difficile* | 027 | gr | gr | gr | gr | gr | >0.5% |
| 26445 | *C. difficile* | 017 | gr | gr | gr | gr | gr | >0.5% |
| 26446 | *C. difficile* | 027 | gr | gr | gr | gr | gr | >0.5% |
| 26447 | *C. difficile* | 001 | gr | gr | gr | gr | gr | >0.5% |
| 26451 | *C. difficile* | 001 | gr | gr | gr | gr | gr | >0.5% |
| 26455 | *C. difficile* | 027 | gr | gr | gr | gr | gr | >0.5% |
| 26457 | *C. difficile* | 027 | gr | gr | gr | gr | gr | >0.5% |
| 26461 | *C. difficile* | 106 | gr | gr | gr | gr | gr | >0.5% |
| 26463 | *C. difficile* | 002 | gr | gr | gr | gr | gr | >0.5% |
| 26466 | *C. difficile* | 020 | gr | gr | gr | gr | gr | >0.5% |
| 26467 | *C. difficile* | 002 | gr | gr | gr | gr | gr | >0.5% |
| 26471 | *C. difficile* | 001 | gr | gr | gr | gr | gr | >0.5% |
| 26472 | *C. difficile* | 014 | gr | gr | gr | gr | gr | >0.5% |
| 26480 | *C. difficile* | 106 | gr | gr | gr | gr | gr | >0.5% |
| 26484 | *C. difficile* | 106 | gr | gr | gr | gr | gr | >0.5% |
| 26485 | *C. difficile* | 078 | gr | gr | gr | gr | gr | >0.5% |
| 26489 | *C. difficile* | 176 | gr | gr | gr | gr | gr | >0.5% |
| 26494 | *C. difficile* | 126 | gr | gr | gr | gr | gr | >0.5% |
| 26500 | *C. difficile* | 014 | gr | gr | gr | gr | gr | >0.5% |
| 26503 | *C. difficile* | 014 | gr | gr | gr | gr | gr | >0.5% |
| 26543 | *C. difficile* | 078 | gr | gr | gr | gr | gr | >0.5% |
| 26544 | *C. difficile* | 078 | gr | gr | gr | gr | gr | >0.5% |
| 26563 | *C. difficile* | 018 | gr | gr | gr | gr | gr | >0.5% |

TABLE 5-continued

In vitro activity of diluent, Na benzoate and Na citrate, and against
Clostridium difficile and other enteric organisms tested by the agar dilution method

| RMA# | organism | Ribotype | diluent 10% | diluent 20% | Na benz 0.02% | Na benz 0.01% | Na benz 0.005% | Na citrate |
|---|---|---|---|---|---|---|---|---|
| 26572 | C. difficile | 017 | gr | gr | gr | gr | gr | >0.5% |
| 21317 | Bif. adolescentis | | gr | gr | gr | gr | gr | >0.5% |
| 21531 | Bif. adolescentis | | gr | gr | gr | gr | gr | >0.5% |
| 21551 | Bif. adolescentis | | gr | gr | gr | gr | gr | >0.5% |
| 21680 | Bif. adolescentis | | gr | gr | gr | gr | gr | >0.5% |
| 21703 | Bif. adolescentis | | gr | gr | gr | gr | gr | >0.5% |
| 26982 | B. fragilis | | gr | gr | gr | gr | gr | >0.5% |
| 26981 | B. fragilis | | gr | gr | gr | gr | gr | >0.5% |
| 26980 | B. fragilis | | gr | gr | gr | gr | gr | >0.5% |
| 26979 | B. fragilis | | gr | gr | gr | gr | gr | >0.5% |
| 26978 | B. fragilis | | gr | gr | gr | gr | gr | >0.5% |
| ATCC 700057 | C. difficile | | gr | gr | gr | gr | gr | >0.5% | gc, growth control
ng, no growth
gr, growth

Discussion: The vancomycin MICs for both preparations were very similar with both producing mostly MICs of 1 or 2 µg/ml with a few isolates at 4 µg/ml. The triplicate MICs were averaged and are shown in a separate column. The diluent at the concentration present in the test (~0.01%) did not show inhibition, and when tested at much higher concentrations of 10% or 20%, also did not show any growth inhibition for any of the strains. Since two of the ingredients in the diluent are Na benzoate and Na citrate, we tested those separately and also saw no inhibition at concentrations exceeding those present in the diluent.

Cutis vancomycin solution is comparable to the standard vancomycin as measured by the agar dilution method. The diluent tested at much higher concentrations (100×-200×) than present in the dilution series showed no antimicrobial activity.

Example 10: In Vitro Activity of Different Preparations of Vancomycin, Na Benzoate, and Diluent Against *Staphylococcus aureus* and Other Enteric Organisms Diluent was mixed 50:50 with MH broth; additional growth control was MH broth mixed 50:50 with water. While *Klebsiella pneumonia*, and *E. coli* grew in the 50% diluent, the buttons were about 50% the diameter of the growth control, suggesting that some inhibition was occurring.

Surprisingly the Cutis diluent or liquid solution of the invention was able to effectively inhibit mold and yeast growth for long periods of time at room temperature without impacting the growth of *C. Diff*.

| RMA# | organism | S-VAN | S-VAN | S-VAN | C-VAN | C-VAN | C-VAN | diluent 50% | GC 50% | Na benz 0.02% | Na benz 0.01% |
|---|---|---|---|---|---|---|---|---|---|---|---|
| 18546 | S. aureus | 1 | 1 | 1 | ng | ng | ng | ng | gr | gr | gr |
| 18547 | S. aureus | 2 | 1 | 1 | ng | ng | ng | ng | gr | gr | gr |
| 18683 | S. aureus | 0.5 | 0.5 | 0.5 | ng | ng | ng | ng | gr | gr | gr |
| 18913 | S. aureus | 1 | 0.5 | 0.5 | ng | ng | ng | ng | gr | gr | gr |
| 19065 | S. aureus | 1 | 1 | 1 | ng | ng | ng | ng | gr | gr | gr |
| 19066 | S. aureus | 0.5 | 0.5 | 0.5 | ng | ng | ng | ng | gr | gr | gr |
| 19831 | S. aureus | 0.5 | 0.5 | 0.5 | ng | ng | ng | ng | gr | gr | gr |
| 19841 | S. aureus | 1 | 1 | 1 | ng | ng | ng | ng | gr | gr | gr |
| 21291 | S. aureus | 0.5 | 0.5 | 0.5 | ng | ng | ng | ng | gr | gr | gr |
| 21743 | S. aureus | 0.5 | 0.5 | 0.5 | ng | ng | ng | ng | gr | gr | gr |
| 22670 | S. aureus | 1 | 0.5 | 0.5 | ng | ng | ng | ng | gr | gr | gr |
| 22727 | S. aureus | 0.5 | 0.5 | 0.5 | ng | ng | ng | ng | gr | gr | gr |
| 22738 | S. aureus | 0.5 | 0.5 | 0.5 | ng | ng | ng | ng | gr | gr | gr |
| 25524 | S. aureus | 1 | 0.5 | 1 | ng | ng | ng | ng | gr | gr | gr |
| 22932 | S. aureus | 2 | 1 | 1 | ng | ng | ng | ng | gr | gr | gr |
| 22934 | S. aureus | 1 | 1 | 1 | ng | ng | ng | ng | gr | gr | gr |
| 22935 | S. aureus | 1 | 1 | 1 | ng | ng | ng | ng | gr | gr | gr |
| 23270 | S. aureus | 1 | 1 | 1 | ng | ng | ng | ng | gr | gr | gr |
| 23271 | S. aureus | 1 | 1 | 1 | ng | ng | ng | ng | gr | gr | gr |
| 23272 | S. aureus | 0.5 | 0.5 | 0.5 | ng | ng | ng | ng | gr | gr | gr |
| 23350 | S. aureus | 1 | 1 | 1 | ng | ng | ng | ng | gr | gr | gr |
| 23351 | S. aureus | 1 | 1 | 1 | ng | ng | ng | ng | gr | gr | gr |
| 23352 | S. aureus | 1 | 0.5 | 1 | ng | ng | ng | ng | gr | gr | gr |
| 23394 | S. aureus | 0.5 | 0.5 | 0.5 | ng | ng | ng | ng | gr | gr | gr |
| 23395 | S. aureus | 1 | 0.5 | 1 | ng | ng | ng | ng | gr | gr | gr |
| 23396 | S. aureus | 0.5 | 0.5 | 0.5 | ng | ng | ng | ng | gr | gr | gr |
| 23397 | S. aureus | 0.5 | 0.5 | 0.5 | ng | ng | ng | ng | gr | gr | gr |
| 23398 | S. aureus | 1 | 1 | 0.5 | ng | ng | ng | ng | gr | gr | gr |
| 23399 | S. aureus | 1 | 1 | 1 | ng | ng | ng | ng | gr | gr | gr |
| 23401 | S. aureus | 0.5 | 0.5 | 0.5 | ng | ng | ng | ng | gr | gr | gr |
| 23502 | S. aureus | 1 | 0.5 | 1 | ng | ng | ng | ng | gr | gr | gr |

-continued

| RMA# | organism | S-VAN | S-VAN | S-VAN | C-VAN | C-VAN | C-VAN | diluent 50% | GC 50% | Na benz 0.02% | Na benz 0.01% |
|---|---|---|---|---|---|---|---|---|---|---|---|
| 23509 | S. aureus |  |  |  | ng | ng | ng | ng | gr | gr | gr |
| 23613 | S. aureus | 1 | 1 | 0.5 | ng | ng | ng | ng | gr | gr | gr |
| 23614 | S. aureus | 1 | 1 | 1 | ng | ng | ng | ng | gr | gr | gr |
| 23615 | S. aureus | 0.5 | 0.5 | 0.5 | ng | ng | ng | ng | gr | gr | gr |
| 23616 | S. aureus | 0.5 | 0.5 | 0.5 | ng | ng | ng | ng | gr | gr | gr |
| 23617 | S. aureus | 0.5 | 0.5 | 0.5 | ng | ng | ng | ng | gr | gr | gr |
| 23618 | S. aureus | 1 | 0.5 | 1 | ng | ng | ng | ng | gr | gr | gr |
| 23619 | S. aureus | 0.5 | 0.5 | 0.5 | ng | ng | ng | ng | gr | gr | gr |
| 23620 | S. aureus | 0.5 | 0.5 | 0.5 | ng | ng | ng | ng | gr | gr | gr |
| 23621 | S. aureus | 1 | 1 | 1 | ng | ng | ng | ng | gr | gr | gr |
| 23622 | S. aureus | 1 | 1 | 1 | ng | ng | ng | ng | gr | gr | gr |
| 23623 | S. aureus | 1 | 1 | 1 | ng | ng | ng | ng | gr | gr | gr |
| 23812 | S. aureus | 1 | 1 | 1 | ng | ng | ng | ng | gr | gr | gr |
| 24160 | S. aureus | 1 | 1 | 1 | ng | ng | ng | ng | gr | gr | gr |
| 24161 | S. aureus | 1 | 1 | 1 | ng | ng | ng | ng | gr | gr | gr |
| 24162 | S. aureus | 0.5 | 0.5 | 0.5 | ng | ng | ng | ng | gr | gr | gr |
| 24163 | S. aureus | 0.5 | 0.5 | 0.5 | ng | ng | ng | ng | gr | gr | gr |
| 24164 | S. aureus | 1 | 0.5 | 0.5 | ng | ng | ng | ng | gr | gr | gr |
| 24463 | S. aureus | 0.5 | 0.5 | 0.5 | ng | ng | ng | ng | gr | gr | gr |
| ATCC | S. aureus | 2 | 2 | 2 | ng | ng | ng | ng | gr | gr | gr |
| ATCC | S. aureus | 2 | 1 | 1 | ng | ng | ng | ng | gr | gr | gr |

Example 11

Stability studies have indicated that Vancomycin HCl Solution is stable when stored in oral syringes. The study was performed on the 25 mg/mL Vancomycin Solution in clear and amber oral syringes. The tests included appearance, pH, and microbial assay (USP <81>). The results indicate that Vancomycin HCl Solution when stored at both refrigerated (2-8° C.) and ambient (25° C./60% RH) conditions are stable for at least 3 days.

| | | Vancomycin HCl Stability in Oral Syringe Results | | | | | |
|---|---|---|---|---|---|---|---|
| | | Time Points | | | | | |
| | | Initial | | | Day 3 | | |
| Sample | Storage | Average Antibiotics Microbial Assay (%) Specification: 90.0 to 115.0% | pH Specification ph 2.5-4.5 | Appearance | Average Antibiotics Microbial Assay (%) Specification: 90.0 to 115.0% | pH Specification ph 2.5-4.5 | Appearance |
| Vancomycin Clear Syringe | 2-8° C. | 102.2 | 3.49 | pale yellow liquid | 101.3 | 3.15 | pale yellow liquid |
| | 25° C./60% RH | 101.2 | 3.47 | pale yellow liquid | 97.9 | 3.16 | pale yellow liquid |
| Vancomycin Amber Syringe | 2-8° C. | 104.4 | 3.42 | pale yellow liquid | 102.2 | 3.12 | pale yellow liquid |
| | 25° C./60% RH | 103.8 | 3.40 | pale yellow liquid | 102.0 | 3.13 | pale yellow liquid |

Example 12

Chemical Analysis at 30 days: Stability studies have indicated that Vancomycin HCl Solution is stable for at least 30 days when stored in HDPE container-closure system when tested using a chemical analysis to assay Vancomycin content. The study was performed on the 25 mg/mL Solution. The results indicate that Vancomycin HCl Solution when stored at refrigerated (2-8° C.) conditions is stable for at least 30 days.

| | | Vancomycin HCl Stability (Chemical Analysis to Assay Vancomycin Content) | |
|---|---|---|---|
| | | Time Points | |
| Sample | Storage | Initial Vancomycin Assay Specification: 90.0-110.0% | Day 30 Vancomycin Assay Specification: 90.0-110.0% |
| Vancomycin 25 mg/ml | 2-8° C. | 97.7% | 96.9% |

Example 13: Dissolution Studies for Three Commercially Available Products: Vancomycin (i.e. Vancomycin Oral Liquid of the Invention, Vancomycin Hydrochloride Powder for Injection, and Vancocin® Capsules)

The studies showed that both vancomycin oral liquid of the invention and vancomycin hydrochloride powder for injection demonstrate the same dissolution profile and are both considered rapidly dissolving (i.e. at least 85% dissolution in 15 mins.; see FIGS. 3 to 6). Vancocin® capsules show a slower dissolution profile compared with the two solution forms (see FIGS. 3 to 6). The dissolution tests was performed with Apparatus II (rotating paddle, 100 rpm) using four media, water, buffer pH 4.5, buffer pH 6.8, and 0.1N HCl and were sampled at 10, 15, 20, 30, 45, and 60 minutes. The dissolution profiles show that both vancomycin oral liquid of the invention and vancomycin hydrochloride powder for injection are more readily available compared with Vancocin® capsules in all four media.

Example 14: Appearance of Lyophilized Vancomycin Hydrochloride Powder in Sterile Water for Injection Compared to the Vancomycin Oral Liquid of the Invention at Ambient and Refrigerated Temperature STERILE WATER
Vancomycin
China (Medisca)
Lot 111058/A
3.84 g/147 ml STERIL WATER (Lot 41-326-DK Hospira Inc.)

| | | 2-8 C. | | | RT | | |
|---|---|---|---|---|---|---|---|
| Time | Days | Appearance | pH | Precipitate | Appearance | pH | Precipitate |
| 0 | Jan. 26, 2015 | Light Yellow | 2.9 | 1 | Light Yellow | 2.8 | 1 |
| 1 | Snow day | | | | | | |
| 2 | Jan. 28, 2015 | Light Yellow | 2.9 | 1 | Light Yellow | 3.0 | 1 |
| 3 | Jan. 29, 2015 | Light Yellow | 2.8 | 1 | Light Yellow | 3.0 | 1 |
| 4 | Jan. 30, 2015 | Light Yellow | 2.9 | 1 | Light Yellow | 2.8 | 1 |
| 5 | Jan. 31, 2015 | Weekend | | | Weekend | | |
| 6 | Feb. 1, 2015 | Weekend | | | Weekend | | |
| 7 | Feb. 2, 2015 | Snow day | | | Snow day | | |
| 8 | Feb. 3, 2015 | Light Yellow | 2.7 | 1 | Light Yellow | 2.7 | 1 |
| 15 | Feb. 10 2015 | Light Yellow | 2.9 | 1 | Light Yellow | 2.9 | 1 |
| 21 | Feb. 17, 2015 | Light Yellow | 2.8 | 1 | Light Yellow | 2.7 | 1 |
| 28 | Feb. 23, 2015 | Light Yellow | 2.9 | 1 | Light Yellow | 2.8 | 1 |
| 35 | Feb. 2, 2015 | Light Yellow | | | Light Yellow | | |
| 36 | Mar. 3, 215 | Light Yellow | | 1 | Light Yellow | | 1 |
| 37 | Mar. 4, 2015 | Light Yellow | | 1 | Light Yellow | | 1 |
| 38 | Mar. 5, 2015 | Light Yellow | | 1 | Light Yellow | | 1 |
| 39 | Mar. 6, 2015 | Light Yellow | | 1 | Light Yellow | | 1 |
| 42 | Mar. 9, 2015 | Light Yellow | | 1 | Light Yellow | | 1 |

SOLUTION OF THE INVENTION
Vancomycin
China (Medisca)
Lot 111058/A
3.84 g/147 ml STERIL WATER (Lot NWA0048)

| | | 2-8 C. | | | RT | | |
|---|---|---|---|---|---|---|---|
| Time | Days | Appearance | pH | Precipitate | Appearance | pH | Precipitate |
| 0 | Jan. 26, 2015 | Clear Golden Yellow to Amber | 2.9 | 1 | Clear Golden Yellow to Amber | 2.9 | 1 |
| 1 | Snow day | | | | | | |
| 2 | Jan. 28, 2015 | Clear Golden Yellow to Amber | 3.1 | 1 | Clear Golden Yellow to Amber | 3.0 | 1 |
| 3 | Jan. 29, 2015 | Clear Golden Yellow to Amber | 2.9 | 1 | Clear Golden Yellow to Amber | 3.0 | 1 |
| 4 | Jan. 30, 2015 | Clear Golden Yellow to Amber | 3.0 | 1 | Clear Golden Yellow to Amber | 3.1 | 1 |
| 5 | Jan. 31, 2015 | Weekend | | | Weekend | | |
| 6 | Feb. 1, 2015 | Weekend | | | Weekend | | |
| 7 | Feb. 2, 2015 | Snow day | | | Snow day | | |
| 8 | Feb. 3, 2015 | Clear Golden Yellow to Amber | 2.9 | 1 | Clear Golden Yellow to Amber | 2.8 | 1 |
| 15 | Feb. 10, 2015 | Clear Golden Yellow to Amber | 2.9 | 1 | Clear Golden Yellow to Amber | 2.9 | 1 |
| 21 | Feb. 17, 2015 | Clear Golden Yellow to Amber | 2.8 | 1 | Clear Golden Yellow to Amber | 2.9 | 1 |
| 28 | Feb. 23, 2015 | Clear Golden Yellow to Amber | 2.9 | 1 | Clear Golden Yellow to Amber | 3.0 | 1 |
| 35 | Mar. 2, 2015 | | | | | | |

SOLUTION OF THE INVENTION
Vancomycin
China (Medisca)
Lot 111058/A
3.84 g/147 ml STERIL WATER (Lot NWA0048)

| | | 2-8 C. | | | RT | | |
|---|---|---|---|---|---|---|---|
| Time | Days | Appearance | pH | Precipitate | Appearance | pH | Precipitate |
| 36 | Mar. 3, 2015 | Clear Golden Yellow to Amber | | 1 | Clear Golden Yellow to Amber | | 1 |
| 37 | Mar. 4, 2015 | Clear Golden Yellow to Amber | | 1 | Clear Golden Yellow to Amber | | 1 |
| 38 | Mar. 5, 2015 | Clear Golden Yellow to Amber | | 1 | Clear Golden Yellow to Amber | | 1 |
| 39 | Mar. 6, 2015 | Clear Golden Yellow to Amber | | 1 | Clear Golden Yellow to Amber | | 1 |
| 42 | Mar. 9, 2015 | Clear Golden Yellow to Amber | | 1 | Clear Golden Yellow to Amber | | 1 |

1 = Free of particles
2 = slightly hazy
3 = small amount of particles visible
4 = large amount of particles visible
5 = completely out of solution

STERILE WATER
Vancomycin
Hungary (Xellia)
Lot B1231901
3.84 g/147ml STERIL WATER (Lot 41-326-DK Hospira Inc.)

| | | 2-8 C. | | | RT | | |
|---|---|---|---|---|---|---|---|
| Time | Days | Appearance | pH | Precipitate | Appearance | pH | Precipitate |
| 0 | Jan. 26, 2015 | Clear | 3.5 | 1 | Clear | 3.4 | 1 |
| 1 | Snow day | | | | | | |
| 2 | Jan. 28, 2015 | Clear | 3.6 | 1 | Clear | 3.6 | 1 |
| 3 | Jan. 29, 2015 | Clear | 3.6 | 1 | Clear | 3.6 | 1 |
| 4 | Jan. 30, 2015 | Clear | 3.3 | 1 | Clear | 3.5 | 1 |
| 5 | Jan. 3Jan. 15 | Weekend | | | Weekend | | |
| 6 | Feb. Jan. 15 | Weekend | | | Weekend | | |
| 7 | Feb. 2, 2015 | Snow day | | | Snow day | | |
| 8 | Feb. 3, 2015 | Clear | 3.4 | 1 | Clear | 3.5 | 1 |
| 15 | Feb. 10, 2015 | Clear | 3.4 | 1 | Clear | 3.6 | 1 |
| 21 | Feb. 17, 2015 | Clear | 3.6 | 1 | Clear | 3.3 | 1 |
| 28 | Feb. 23, 2015 | Clear | 3.5 | 1 | Clear | 3.9 | 1 |
| 35 | Mar. 2, 2015 | Clear | | 1 | | | 2 |
| 36 | Mar. 3, 2015 | Clear | | 1 | | | 3 |
| 37 | Mar. 4, 2015 | Clear | | 1 | | | 3 |
| 38 | Mar. 5, 2015 | Clear | | 1 | | | 4 |
| 39 | Mar. 6, 2015 | Clear | | 1 | | | 4 |
| 42 | Mar. 9, 2015 | Clear | | 1 | | | 5 |

SOLUTION OF THE INVENTION
Vancomycin
Hungary (Xellia)
Lot B1231901
3.84 g/147 ml STERIL WATER (Lot NWA0048)

| | | 2-8 C. | | | RT | | |
|---|---|---|---|---|---|---|---|
| Time | Days | Appearance | pH | Precipitate | Appearance | pH | Precipitate |
| 0 | Jan. 26, 2015 | Clear Golden Yellow to Amber | 3.3 | 1 | Clear Golden Yellow to Amber | 3.3 | 1 |
| 1 | Snow day | | | | | | |
| 2 | Jan. 28, 2015 | Clear Golden Yellow to Amber | 3.4 | 1 | Clear Golden Yellow to Amber | 3.5 | 1 |
| 3 | Jan. 29, 2015 | Clear Golden Yellow to Amber | 3.5 | 1 | Clear Golden Yellow to Amber | 3.5 | 1 |

SOLUTION OF THE INVENTION
Vancomycin
Hungary (Xellia)
Lot B1231901
3.84 g/147 ml STERIL WATER (Lot NWA0048)

| | | 2-8 C. | | | RT | | |
|---|---|---|---|---|---|---|---|
| Time | Days | Appearance | pH | Precipitate | Appearance | pH | Precipitate |
| 4 | Jan. 30, 2015 | Clear Golden Yellow to Amber | 3.5 | 1 | Clear Golden Yellow to Amber | 3.5 | 1 |
| 5 | Jan. 31, 2015 | Weekend | | | Weekend | | |
| 6 | Feb. 1, 15 | Weekend | | | Weekend | | |
| 7 | Feb. 2, 2015 | Snow day | | | Snow day | | |
| 8 | Feb. 3, 2015 | Clear Golden Yellow to Amber | 3.2 | 1 | Clear Golden Yellow to Amber | 3.2 | 1 |
| 15 | Feb. 10, 2015 | Clear Golden Yellow to Amber | 3.3 | 1 | Clear Golden Yellow to Amber | 3.5 | 1 |
| 21 | Feb. 17, 2015 | Clear Golden Yellow to Amber | 3.2 | 1 | Clear Golden Yellow to Amber | 3.3 | 1 |
| 28 | Feb. 23, 2015 | Clear Golden Yellow to Amber | 3.3 | 1 | Clear Golden Yellow to Amber | 3.4 | 1 |
| 35 | Mar. 2, 2015 | Clear Golden Yellow to Amber | | 1 | Clear Golden Yellow to Amber | | 1 |
| 36 | Mar. 3, 2015 | Clear Golden Yellow to Amber | | 1 | Clear Golden Yellow to Amber | | 1 |
| 37 | Mar. 4, 2015 | Clear Golden Yellow to Amber | | 1 | Clear Golden Yellow to Amber | | 1 |
| 38 | Mar. 5, 2015 | Clear Golden Yellow to Amber | | 1 | Clear Golden Yellow to Amber | | 1 |
| 39 | Mar. 6, 2015 | Clear Golden Yellow to Amber | | 1 | Clear Golden Yellow to Amber | | 1 |
| 42 | Mar. 9, 2015 | Clear Golden Yellow to Amber | | 1 | Clear Golden Yellow to Amber | | 1 |

STERILE WATER
Vancomycin
Denmark (Xellia)
Lot A 3330040
3.84 g/147 ml STERIL WATER (Lot 41-326-DK Hospira Inc.)

| | | 2-8 C. | | | RT | | |
|---|---|---|---|---|---|---|---|
| Time | Days | Appearance | pH | Precipitate | Appearance | pH | Precipitate |
| 0 | Jan. 26, 2015 | Light Pink | 3.8 | 1 | Light Pink | 3.2 | 1 |
| 1 | Snow day | | | | | | |
| 2 | Jan. 28, 2015 | Light Pink | 3.4 | 1 | Light Pink | 3.5 | 1 |
| 3 | Jan. 29, 2015 | Light Pink | 3.3 | 1 | Ligiht Pink | 3.5 | 1 |
| 4 | Jan. 30, 2015 | | | | | | |
| 5 | Jan. 31, 2015 | Weekend | | | Weekend | | |
| 6 | Feb. 1, 2015 | Weekend | | | Weekend | | |
| 7 | Feb. 2, 2015 | Snow day | | | Snow day | | |
| 8 | Feb. 3, 2015 | Light Pink | 3.2 | 1 | Light Pink | 3.2 | 1 |
| 15 | Feb. 10, 2015 | Light Pink | 3.3 | 1 | Light Pink | 3.4 | 1 |
| 21 | Feb. 17, 2015 | Light Pink | 3.2 | 1 | Light Pink | 3.1 | 1 |
| 28 | Feb. 23, 2015 | Light Pink | 3.1 | 1 | Light Pink | 3.5 | 1 |
| 35 | Mar. 2, 2015 | Light Pink | | 1 | | | 1 |
| 36 | Mar. 3, 2015 | Light Pink | | 1 | | | 1 |
| 37 | Mar. 4, 2015 | Light Pink | | 1 | | | 2 |
| 38 | Mar. 5, 2015 | Light Pink | | 1 | | | 3 |
| 39 | Mar. 6, 2015 | Light Pink | | 1 | | | 3 |
| 42 | Mar. 9, 2015 | Light Pink | | 1 | | | 5 |

| SOLUTION OF THE INVENTION<br>Vancomycin<br>Denmark (Xellia)<br>Lot A 3330040<br>3.84 g/147 ml STERIL WATER (Lot NWA0048) |||||||
|---|---|---|---|---|---|---|
| | | 2-8 C. | | | RT | |
| Time | Days | Appearance | pH | Precipitate | Appearance | pH | Precipitate |
| 0 | Jan. 26, 2015 | Clear Golden Yellow to Amber | 3.4 | 1 | Clear Golden Yellow to Amber | 3.3 | 1 |
| 1 | Snow day | | | | | | |
| 2 | Jan. 28, 2015 | Clear Golden Yellow to Amber | 3.4 | 1 | Clear Golden Yellow to Amber | 3.4 | 1 |
| 3 | Jan. 29, 2015 | Clear Golden Yellow to Amber | 3.4 | 1 | Clear Golden Yellow to Amber | 3.4 | 1 |
| 4 | Jan. 30, 2015 | | | | | | |
| 5 | Jan. 31, 2015 | Weekend | | | Weekend | | |
| 6 | Feb. 1, 15 | Weekend | | | Weekend | | |
| 7 | Feb. 2, 2015 | Snow day | | | Snow day | | |
| 8 | Feb. 3, 2015 | Clear Golden Yellow to Amber | 3.2 | 1 | Clear Golden Yellow to Amber | 3.2 | 1 |
| 15 | Feb. 10, 2015 | Clear Golden Yellow to Amber | 3.3 | 1 | Clear Golden Yellow to Amber | 3.3 | 1 |
| 21 | Feb. 17, 2015 | Clear Golden Yellow to Amber | 3.1 | 1 | Clear Golden Yellow to Amber | 3.2 | 1 |
| 28 | Feb. 23, 2015 | Clear Golden Yellow to Amber | 3.2 | 1 | Clear Golden Yellow to Amber | 3.4 | 1 |
| 35 | Mar. 2, 2015 | | | | | | |
| 36 | Mar. 3, 2015 | Clear Golden Yellow to Amber | | 1 | Clear Golden Yellow to Amber | | 1 |
| 37 | Mar. 4, 2015 | Clear Golden Yellow to Amber | | 1 | Clear Golden Yellow to Amber | | 1 |
| 38 | Mar. 5, 2015 | Clear Golden Yellow to Amber | | 1 | Clear Golden Yellow to Amber | | 1 |
| 39 | Mar. 6, 2015 | Clear Golden Yellow to Amber | | 1 | Clear Golden Yellow to Amber | | 1 |
| 42 | Mar. 9, 2015 | Clear Golden Yellow to Amber | | 1 | Clear Golden Yellow to Amber | | 1 |

Example 15: Caco-2 Permeability Study

Caco-2 cells are used as an in vitro model of the human intestinal epithelium and permit assessment of the intestinal permeability of potential drugs. Vancomycin is added to either the apical or basolateral side of a confluent monolayer of Caco-2 cells and permeability is measured by monitoring the appearance of the Vancomycin on the opposite side of the monolayer using LC-MS/MS. When performing a bi-directional assay, the efflux ratio (ER) is calculated from the ratio of B→A and A→B permeabilities.

The permeability measure of vancomycin in the apical to basolateral (A→B) and basolateral to apical (B→A) direction across Caco-2 cells, and to determine the efflux ratio. Three different commercially available products of vancomycin were tested at a pH of 5.7, 6.5, and 7.4: vancomycin oral liquid of the invention, lyophilized vancomycin hydrochloride powder for injection in solution, and vancomycin hydrochloride capsules. Listed in the table below are the preliminary data for the Papp rate coefficients of these test articles (at the indicated pH values).

| Test Article | mean A->B Papp (×10−6 cm s−1) | mean B->A Papp (×10−6 cm s−1) |
|---|---|---|
| Ranitidine | 0.3 | 1.5 |
| Talinolol | 0.1 | 10.2 |
| Metoprolol | 11.6 | 30.0 |
| Vancomycin Oral Liquid of the Invention @ pH 5.7 | <0.3 | <0.3 |
| Vancomycin Injection @ pH 5.7 | <0.3 | <0.3 |
| Vancomycin Capsule @ pH 5.7 | <0.3 | <0.3 |
| Vancomycin Oral Liquid of the Invention @ pH 6.5 | <0.3 | <0.3 |
| Vancomycin Injection @ pH 6.5 | <0.3 | <0.3 |
| Vancomycin Capsule @ pH 6.5 | <0.3 | <0.3 |
| Vancomycin Oral Liquid of the Invention @ pH 7.4 | <0.3 | <0.3 |
| Vancomycin Injection @ pH 7.4 | <0.3 | <0.3 |
| Vancomycin Capsule @ pH 7.4 | <0.86 | <0.3 |

REFERENCES

U.S. Pat. No. 4,670,258 to Harris et al.

Fraser T G, Swiencicki J F. *Clostridium Difficile*. In: Cleveland Clinic: Center for continuting education. <http://www.clevelandclinicmeded.com/medicalpubs/disease-management/infectious-disease/clostridum-difficile-infection/>. Accessed Aug. 15, 2013.

Ryan K J, Ray C G. Sherris *Medical Microbiology* (4th ed.). McGraw Hill. 2004. 322-4.

Hall I C, O'Toole E. Intestinal flora in newborn infants with a description of a new pathogenic anaerobe, *Bacillus difficilis*. *Am J Dis Child*. 1935; 49:390-402.

Baron E J, Tenover F C. The emerging threat of *Clostridium difficile* infection. <http://www.cepheid.com/media/files/brochures/CDiff>. Accessed Aug. 15, 2013.

Bartlett, J G. Narrative review: the new epidemic of *Clostridium difficile*-associated enteric disease. *Ann Intern Med.* 2006; 145:758.

Weir E., Flegel K. Protecting against *Clostridium difficile* illness. *Can Med Assoc J.* 2005; 172:1178.

Pawar D, Bhandari P, Allenby K. A Review: *Clostridium Difficile*-Associated Diarrhea. *Indian Medical Gazette.* 2011.

CDC. Sehulster L, Chinn R Y W. Guidelines for environmental infection control in healthcare facilities. *MMWR.* 2003; 52(RR10); 1-42.

Hull M W, Beck P L. *Clostridium difficile*-associated colitis. *Can Fam Physician.* 2004; 50:1536-40, 1543-5.

Bartlett, J G. The Case for Vancomycin as the Preferred Drug for Treatment of *Clostridium difficile* Infection. *CID.* 2008; 46:1489-1492.

Johnson S. Homann S R, Bettin K M, et al. Treatment of asymptomatic *Clostridium difficile* carriers (fecal excretors) with vancomycin or metronidazole: a randomized, placebo-controlled trial. *Ann Intern Med.* 1992; 117:297-302.

Gennaro A R. *Remington: The Science and Practice of Pharmacy.* Lippincott Williams & Wilkins. 20$^{th}$ Ed: 1018-1021. 2000.

Burdock G A. *Fenaroli's Handbook of Flavor Ingredients.* Cleveland: CRC. 1994.

U.S. Pharmacist. Vancomycin Survey Results. March 2013.

P\S\L Research. Pharmacist Compounding Study. October 2012.

Mallet L, Sesin G P, Ericson J, et al. Storage of vancomycin oral solution. *N Engl J Med.* 1982; 307(7): 445.

Vancomycin Hydrochloride for Injection, USP Fliptop Vial For Intravenous Use (product insert). Hospira. Accessed Jan. 10, 2014.

Instar Research. Vancomycin Volume Study. April 2013.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A non-sterile stable liquid formulation formulated for oral administration, consisting of:
   (a) 0.1-0.4% w/v citric acid,
   (b) water,
   (c) a sweetener,
   (d) a preservative, wherein the preservative is selected from the group consisting of ascorbic acid, ascorbyl palmitate, benzyl alcohol, butylated hydroxyanisole, butylated hydroxytoluene, erythorbic acid, fumaric acid, malic acid, propyl gallate, sodium ascorbate, sodium benzoate, sodium bisulfate, sodium metabisulfite, sodium sulfite, parabens, benzoic acid, potassium sorbate, and vanillin,
   (e) vancomycin hydrochloride, and
   (f) flavoring agent,
   wherein the non-sterile stable liquid formulation is homogenous and stable for at least 1 week at ambient and refrigerated temperature and has a pH of 25-4.5.

2. The liquid formulation of claim 1, wherein the citric acid is 0.12% w/v.

3. The liquid formulation of claim 1, wherein the sweetener is 0.1-0.3% w/v.

4. A non-sterile stable liquid formulation formulated for oral administration, consisting of:
   (a) 0.1-0.4% w/v citric acid,
   (b) water,
   (c) a sweetener,
   (d) a preservative, wherein the preservative is selected from the group consisting of benzyl alcohol, sodium benzoate, parabens, benzoic acid, and potassium sorbate,
   (e) vancomycin hydrochloride, and
   (f) flavoring agent,
   wherein the non-sterile stable liquid formulation is homogenous and stable for at least 1 week at ambient and refrigerated temperature and has a pH of 2.5-4.5.

5. The liquid formulation of claim 4, wherein the citric acid is 0.12% w/v.

6. The liquid formulation of claim 4, wherein the sweetener is 0.1-0.3% w/v.

7. A method of treating *Clostridium difficile* pseudomembranous colitis or Staphylococcal enterocolitis in a subject comprising administering a vancomycin oral liquid composition to the subject in a therapeutically effective amount, wherein the vancomycin oral liquid composition consists of:
   (a) 0.1-0.4% w/v citric acid,
   (b) water,
   (c) a sweetener,
   (d) a preservative,
   wherein the preservative is selected from the group consisting of benzyl alcohol, sodium benzoate, parabens, benzoic acid, and potassium sorbate,
   (e) vancomycin hydrochloride, and
   (f) flavoring agent,
   wherein the vancomycin oral liquid composition is homogenous and stable for at least 1 week at ambient and refrigerated temperature and has a pH of 2.5-4.5.

8. The method of claim 7, wherein the preservative is sodium benzoate.

9. The method of claim 7, wherein the sweetener is 0.1-0.3% w/v.

10. The method of claim 7, wherein the flavoring agent is a berry flavor.

* * * * *

UNITED STATES PATENT AND TRADEMARK OFFICE
CERTIFICATE OF CORRECTION

PATENT NO. : 10,959,949 B2
APPLICATION NO. : 16/941414
DATED : March 30, 2021
INVENTOR(S) : Indu Muni et al.

It is certified that error appears in the above-identified patent and that said Letters Patent is hereby corrected as shown below:

In the Claims

At Column 46, Claim 1, Line 10:
\*\*and refrigerated temperature and has a pH of 25-4.5.\*\*
Should be:
–and refrigerated temperature and has a pH of 2.5-4.5–

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*